United States Patent
Ince et al.

(10) Patent No.: US 9,730,988 B2
(45) Date of Patent: Aug. 15, 2017

(54) PARASITIC BIOLOGICAL AGENTS FOR TREATMENT AND PREVENTION OF GRAFT VERSUS HOST DISEASE

(71) Applicant: University of Iowa Research Foundation, Iowa City, IA (US)

(72) Inventors: Mirac Nedim Ince, Iowa City, IA (US); David E. Elliott, North Liberty, IA (US); George J. Weiner, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 18 days.

(21) Appl. No.: 14/683,778

(22) Filed: Apr. 10, 2015

(65) Prior Publication Data
US 2016/0045581 A1    Feb. 18, 2016

Related U.S. Application Data

(60) Provisional application No. 61/978,118, filed on Apr. 10, 2014.

(51) Int. Cl.
| | |
|---|---|
| *A61K 39/00* | (2006.01) |
| *G01N 33/68* | (2006.01) |
| *G01N 33/50* | (2006.01) |
| *G01N 33/569* | (2006.01) |

(52) U.S. Cl.
CPC ........ *A61K 39/0003* (2013.01); *A61K 39/001* (2013.01); *G01N 33/505* (2013.01); *G01N 33/56972* (2013.01); *G01N 33/6863* (2013.01); *G01N 33/6866* (2013.01); *A61K 2039/577* (2013.01); *A61K 2039/58* (2013.01); *G01N 2333/525* (2013.01); *G01N 2333/57* (2013.01); *G01N 2800/245* (2013.01); *G01N 2800/52* (2013.01)

(58) Field of Classification Search
CPC .. G01N 38/00; G01N 38/21; G01N 2039/522; G01N 2039/5254; G01N 33/5008; G01N 33/5032; G01N 33/5047; G01N 33/505
See application file for complete search history.

(56) References Cited

U.S. PATENT DOCUMENTS

2012/0177645 A1* 7/2012 Langermann ...... A61K 38/1709
424/134.1

OTHER PUBLICATIONS

Liwski et al., (Transplantation. vol. 69(9), May 15, 2000, pp. 1912-1922).*
Beres, et al., "CD8+ Foxp3+ Regulatory T Cells are Induced During Graft-Versus-Host Disease and Mitigate Disease Severity," *J. Immunol.*, vol. 189, No. 1, pp. 464-474, Jul. 2012.
(Continued)

*Primary Examiner* — Ja'Na Hines
(74) *Attorney, Agent, or Firm* — Sunstein Kann Murphy & Timbers LLP

(57) ABSTRACT

The invention relates to helminthic parasite preparations and their use for treatment or prevention of GVHD in a subject that has undergone a transplant. The invention also related to helminthic parasite preparations and their use for prevention of GVHD in a subject prior to a transplant.

20 Claims, 15 Drawing Sheets

(56) References Cited

OTHER PUBLICATIONS

Cohen, et al., "The Role of CD4$^+$CD25$^{hi}$ Regulatory T Cells in the Physiopathogeny of Graft-Versus-Host Disease," *Curr. Opinion in Immunol.*, vol. 18, Issue 5, pp. 580-585, Oct. 1, 2006.

Ferrara, et al., "Graft-Versus-Host Disease," *The Lancet*, vol. 373, Issue 9674, pp. 1550-1561, May 2, 2009.

Gooley, et al., "Reduced Mortality After Allogeneic Hematopoietic-Cell Transplantation," *N. Engl., J. Med.*, vol. 363, No. 22, pp. 2091-2101, Nov. 2010.

Hoffman, et al., "Donor-Type CD4$^+$CD25$^+$ Regulatory T Cells Suppress Lethal Acute Graft-Versus-Host Disease After Allogeneic Bone Marrow Transplantation," *J. Exp. Med.*, vol. 196, No. 3, pp. 389-399, 2002.

Izcue, et al., "Regulatory T Cells Suppress Systemic and Mucosal Immune Activation to Control Intestinal Inflammation," *Immunol. Rev.*, vol. 212, pp. 256-271, Aug. 2006.

Kohrt, et al., "NKT Cells, Treg, and Their Interactions in Bone Marrow Transplantation," *Eur. J. Immunol.*, vol. 40, pp. 1862-1869, 2010.

Nguyen, et al., "Role of Naturally Arising Regulatory T Cells in Hematopoietic Cell Transplantation," *Biology of Blood and Marrow Transplantation*, vol. 12, pp. 995-1009, 2006.

Shevach, E., "Mechanisms of Foxp3$^+$ T Regulatory Cell-Mediated Suppression," *Immunity Review*, vol. 30, pp., 636-645, May 2009.

Shlomchik, W., "Graft-Versus-Host Disease," *Nature Reviews Immunology*, vol. 7, pp. 340-352, May 2007.

Socié, et al., "Acute Graft-Versus-Host Disease: From the Bench to the Bedside," *Blood*, vol. 114, No. 20, pp. 4397-4336, Nov. 2009.

Taylor, et al., "The Infusion of Ex Vivo Activated and Expanded CD4$^+$CD25$^+$ Immune Regulatory Cells Inhibits Graft-Versus-Host Disease Lethality," *Blood*, vol. 99, No. 10, pp. 3493-3499, May 2002.

Wing, et al., "Regulatory T Cells Exert Checks and Balances on Self Tolerance and Autoimmunity," *Nature Immunology*, vol. 11, No. 1, pp. 7-13, 2010.

\* cited by examiner

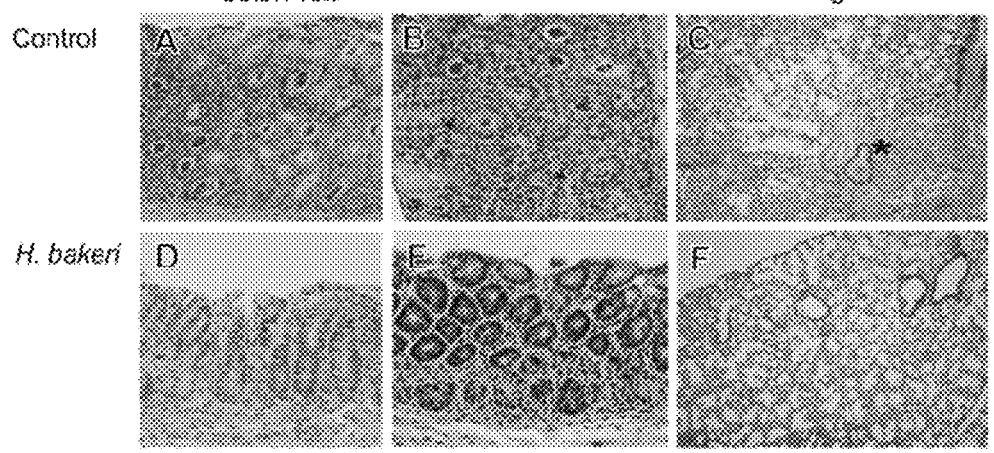
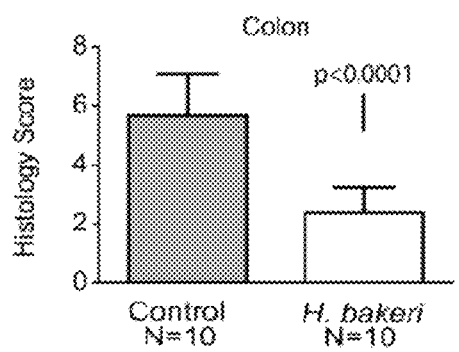
Fig. 2G
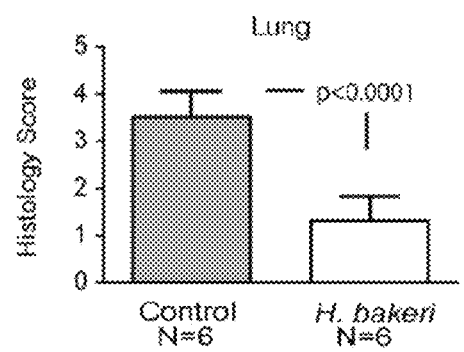
Fig. 2H

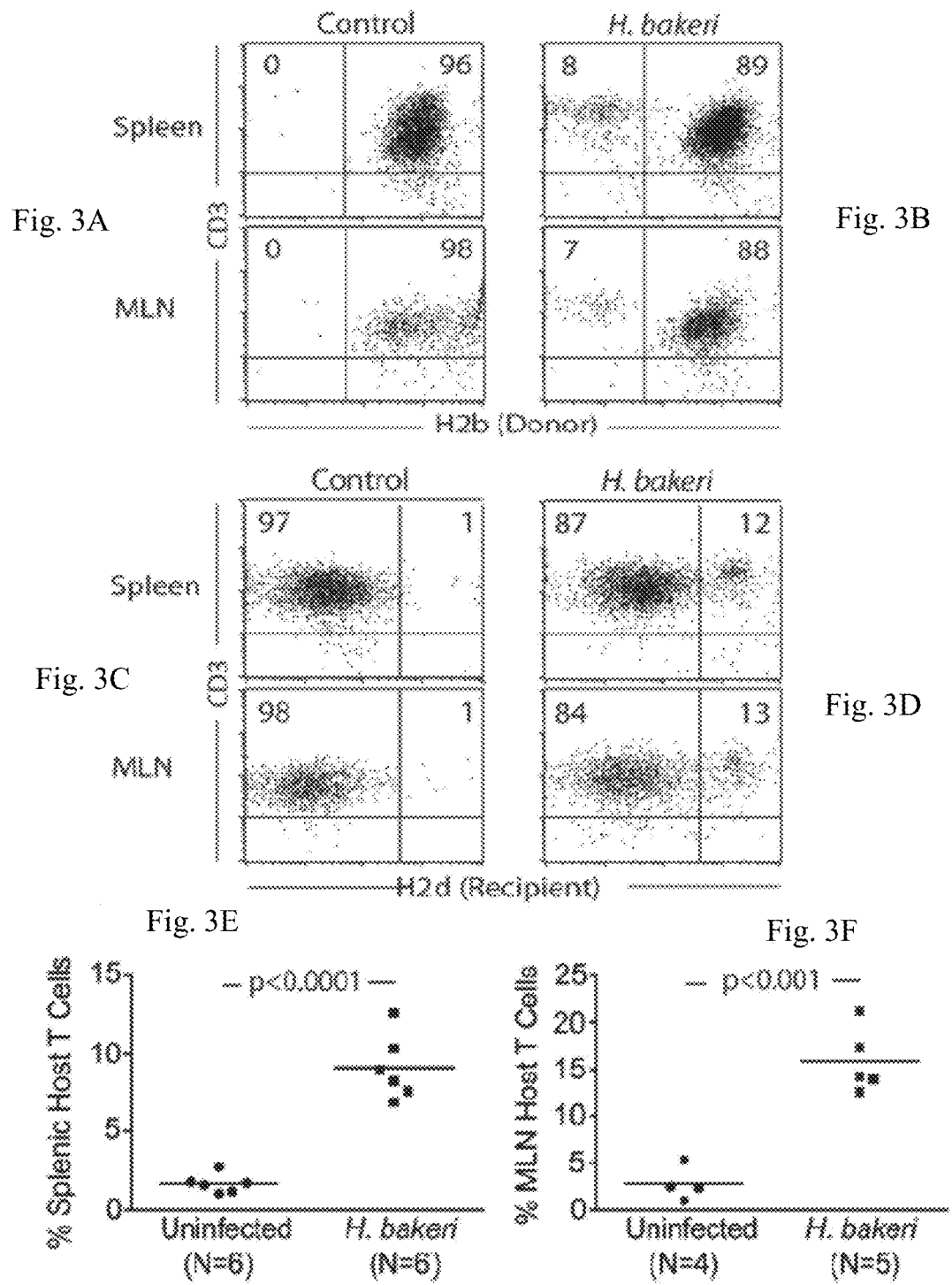

Uninfected Colon
Balb/C Mouse
no BMT

*H. bakeri* Colon
Balb/C Mouse
no BMT

Uninfected Lung
Balb/C Mouse
no BMT

*H. bakeri* Lung
Balb/C Mouse
no BMT

Fig. 11A
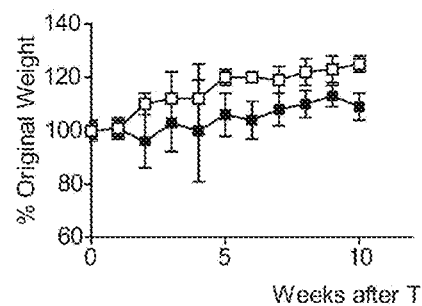
Fig. 11B
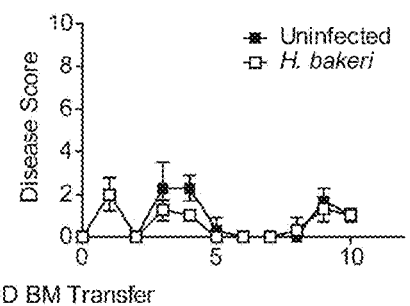
Weeks after TCD BM Transfer
Fig. 11C
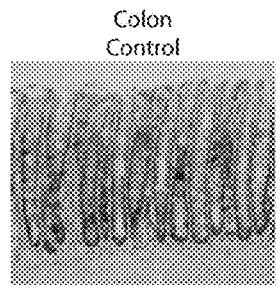
Fig. 11D
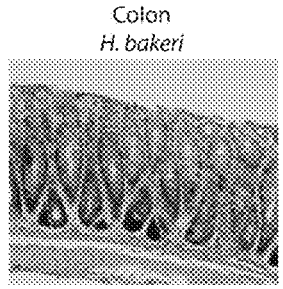
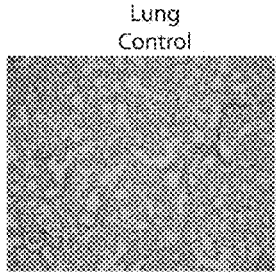
Fig. 11E
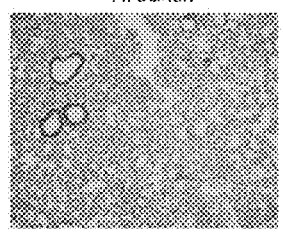
Fig. 11F

Figure 14
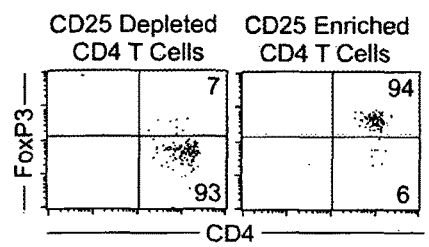
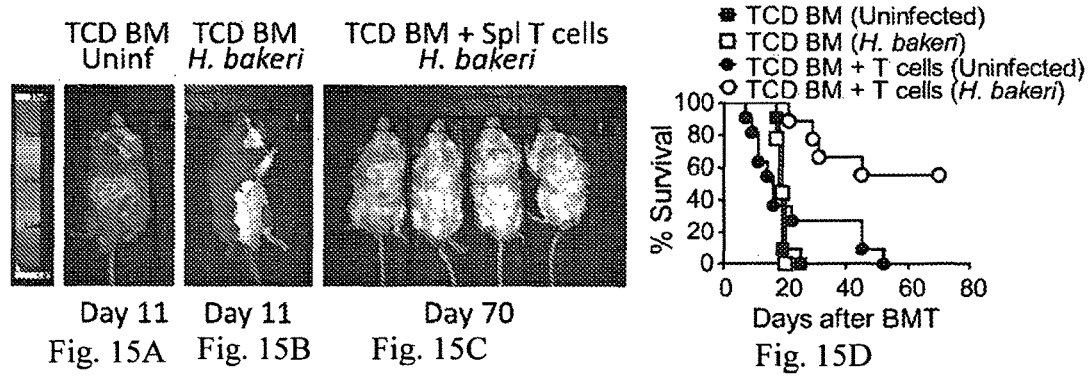
Day 11 | Day 11 | Day 70
Fig. 15A | Fig. 15B | Fig. 15C
Fig. 15D

PARASITIC BIOLOGICAL AGENTS FOR TREATMENT AND PREVENTION OF GRAFT VERSUS HOST DISEASE

RELATED APPLICATIONS

This application claims priority to U.S. provisional application Ser. No. 61/978,118, filed Apr. 10, 2014. The entire contents of the aforementioned patent application are incorporated herein by this reference.

This invention was made with government support under DK082913, CA097274, AI034495, AI116715, and HL056067 awarded by the National Institute of Health and ACS-IRG-77-004-31 awarded by the American Cancer Society administered through the Holden Comprehensive Cancer Center at the University of Iowa, and by Veterans Administration (VA) Merit Award BX001931. The government has certain rights in the invention.

FIELD OF THE INVENTION

The invention relates to parasite preparations and their use in treatment and prevention of GVHD in subjects that have undergone a transplant.

BACKGROUND OF THE INVENTION

Graft versus host disease (GVHD) is a major and potentially severe complication of bone marrow transplantation in leukemia, lymphoma, myeloma patients as well as in individuals with various other hematological and nonhematological diseases. The disease is mediated by allo-reactivity of donor T lymphocytes to recipient major or minor histocompatibility antigens (Shlomchik W D. Nat. Rev. Immunol. 2007; 7:340-352; Socie G, Blazar B R. Blood 2009; 114:4327-4336.). While the acute form of GVHD affects the skin, intestine and liver, chronic GVHD exhibits multi-organ infiltration similar to various autoimmune diseases (Ferrara J L, Levine J E, Reddy P, Holler E. Lancet 2009; 373:1550-1561).

GVHD is controlled by various immune modulatory mechanisms that include regulatory T cells (Treg) that suppress inflammation driven by effector T lymphocytes (1;10-12). Tregs express the transcription factor FoxP3 and contribute to intestinal immune regulation by cell contact-dependent mechanisms or by the production of modulating cytokines, such as IL10 and TGFβ (Shlomchik, Supra; Izcue, A., et al. 2006. *Immunol. Rev.*:256-271; 13. Cohen, J. L., and Boyer, O. 2006. *Curr. Opin. Immunol.*: 580-585; Wing, K., and Sakaguchi, S. 2010. *Nat. Immunol.*:7-13; Shevach, E. M. 2009. *Immunity.*:636-645; Beres, A. J., Haribhai, D., Chadwick, A. C., Gonyo, P. J., Williams, C. B., and Drobyski, W. R. 2012 *J. Immunol.*:464-474).

Although GVHD can be prevented by depleting donor T cells from the graft, recipients then are predisposed to severe infectious diseases and have a high risk of tumor recurrence because the donor T cells are critical in controlling tumor recurrence. Engraftment as well as the graft versus tumor effect may be diminished by donor T cell removal (Shlomchik, Supra; Kohrt H E, Pillai A B, Lowsky R, Strober S. Eur. J. Immunol. 2010; 40:1862-1869; Gooley T A, Chien J W, Pergam S A et al. N. Engl. J. Med. 2010; 363:2091-2101). In preclinical mouse models, several laboratories have shown that GVHD can be prevented by co-administration of donor's conventional T cells and Tregs given in equal numbers (Kohrt et al. Supra; Nguyen V H, Zeiser R, Negrin R S. Biol. Blood Marrow Transplant. 2006; 12:995-1009; Hoffmann P, Ermann J, Edinger M, Fathman C G, Strober S. J. Exp. Med. 2002; 196:389-399; Taylor P A, Lees C J, Blazar B R Blood 2002; 99:3493-3499).

There is a need in the art for methods of treating or preventing GVHD and reducing GVHD-related morbidity and mortality while preserving the graft versus tumor (GVT) effect of the donor T cells on elimination of a tumor of the recipient.

SUMMARY OF THE INVENTION

The invention provides methods of decreasing the production of IFNγ and/or TNFα by donor T cells from a subject that has received a transplant, by administering a helminthic parasite preparation. Also provided are methods of using helminthic preparations to decrease the level of IFNγ and/or TNFα in the serum of a subject that has received a transplant. The invention also provides for methods of increasing the number of latency associated protein (LAP) expressing donor and/or recipient T cells in a subject that has received a transplant, by administering a helminthic parasite preparation to the subject. The invention also relates to methods of increasing the number and/or percent of FoxP3+ donor and/or recipient derived regulatory T cells in a subject that has received a transplant by administering a helminthic parasite preparation to the subject.

The invention also provides methods of treating or preventing GVHD in a subject that has received or will receive a transplant, for example a stem cell or bone marrow transplant, while preserving the GVT effect of the donor T cells on elimination of a tumor of the recipient.

The invention provides for a method of decreasing the production of IFNγ and/or TNFα by donor regulatory T cells from a subject that has received a transplant, comprising administering a helminthic parasite preparation to the subject in an amount and for a time effective to decrease the production.

The invention also provides for a method of decreasing the level of IFNγ and/or TNFα in the serum of a subject that has received a transplant, comprising administering a helminthic parasite preparation to the subject in an amount and for a time effective to decrease the level.

The invention also provides for a method of increasing the number of latency associated protein (LAP) expressing donor and/or recipient regulatory T cells in a subject that has received a transplant, comprising administering a helminthic parasite preparation to the subject in an amount and for a time effective to increase the number.

The invention also provides for a method of increasing the number and/or percent of FoxP3+ donor and/or recipient derived regulatory T cells in a subject that has received a transplant, comprising administering a helminthic parasite preparation to the subject in an amount and for a time effective to increase the number and/or percent.

In one embodiment, there is an increase in the number and/or percent of FoxP3+ donor and/or recipient derived regulatory T cells in the spleen and/or mesenteric lymph nodes of the subject.

In one embodiment the increase in the number and/or percent of FoxP3+ donor and/or recipient derived regulatory T cells requires STATE.

In another embodiment, the parasite preparation is administered daily, weekly, bi-weekly or every two weeks after the transplant or wherein the parasite preparation is administered in decreasing intervals of time following the transplant. In one embodiment, the parasite preparation is administered once a month for 2 months or more (for example 3 months, 4 months, 5 months, 6 months, 7 months, 8 months, 9 months, 10 months, 11 months, 12 months, 18 months, 24 months, 3 years, 4 years or more) wherein administration is then modified such that the parasite preparation is administered once every other month, every third month etc. Modification of the treatment region is determined by evaluation of the GVHD symptoms disclosed herein.

In one embodiment, administration is continued for at least 6 months. In another embodiment, administration is continued for more than 6 months, for example, 7 months, 8 months, 9 months, 10 months, 11 months, 12 months, 18 months, 24 months, 3 years, 4 years or more, for example, 5, 6, 7, 8, 9, or 10 years. In certain embodiments, administrated is continued for the life of a subject.

In one embodiment, the parasite preparation is administered to the subject after the subject has developed graft versus host disease (GVHD).

The invention also provides for a method of treating Graft Versus Host Disease (GVHD) in a subject that has received a transplant comprising administering a helminthic parasite preparation to the subject after the transplant wherein following the administration there is a decrease in the level of production of IFNγ and/or TNFα by donor regulatory cells isolated from the subject after the transplant, and/or a decrease in the level of IFNγ and/or TNFα in the serum of the subject, thereby treating GVHD.

In one embodiment, the level of production of IFNγ and/or TNFα by donor regulatory T cells, and/or the level of IFNγ and/or TNFα in the serum of the subject is measured prior to administration and after administration of the parasite preparation.

The invention also provides for a method of treating Graft Versus Host Disease (GVHD) in a subject that has received a transplant comprising administering a helminthic parasite preparation to the subject after the transplant wherein following the administration there is an increase in the number of recipient LAP expressing regulatory T cells or donor LAP expressing regulatory T cells, wherein the donor regulatory T cells are isolated from the subject after the transplant, thereby treating GVHD.

In another embodiment, the number of LAP expressing donor and/or recipient regulatory T cells of the subject is measured prior to administration and after administration of the parasite preparation.

In another embodiment, the parasite preparation is administered daily, weekly, bi-weekly or every two weeks after the transplant or wherein the parasite preparation is administered in decreasing intervals of time following the transplant.

In another embodiment, treatment is continued for at least 6 months after transplant.

In another embodiment, GVHD is acute or chronic.

In another embodiment, GVHD is treated if following administration, the subject does not have an onset of one or more of a symptom of GVHD selected from the group consisting of: skin rash, diarrhea, liver disease, weight loss/anorexia, nausea, and vomiting.

In another embodiment, GHVD is treated if following administration there is no increase in the level of IFNγ in the serum of the subject.

In another embodiment, GVHD is treated if following administration of a helminthic parasite preparation there is no increase in the level of IFNγ in the serum of the subject and no onset of a symptom of GVHD selected from the group consisting of: skin rash, diarrhea, liver disease, weight loss/anorexia, nausea, and vomiting.

In another embodiment, GVHD is treated if following administration, there are no detectable apoptotic bodies in tissue derived from the upper gastrointestinal tract.

The invention also provides for a method of preventing GVHD in a subject that has received a transplant comprising administering a helminthic parasite preparation to the subject after the transplant, wherein following the administration there is no increase in the level of IFNγ and/or TNFα in the serum of the subject, thereby preventing GVHD.

In another embodiment, GVHD is treated if, following administration, the subject does not have an onset of one or more of a symptom of GVHD selected from the group consisting of: skin rash, diarrhea, liver disease, weight loss/anorexia, nausea, and vomiting.

In another embodiment, GHVD is treated if following administration there is no increase in the level of IFNγ in the serum of the subject.

In another embodiment, GVHD is treated if following administration there is no increase in the level of IFNγ in the serum of the subject and no onset of a symptom of GVHD selected from the group consisting of: skin rash, diarrhea, liver disease, weight loss/anorexia, nausea, and vomiting.

In another embodiment, GVHD is treated if following administration of a helminthic parasite preparation, there are no detectable apoptotic bodies in tissue derived from the upper gastrointestinal tract.

In another embodiment, a graft versus tumor effect is observed in the subject being treated.

In another embodiment, a graft versus leukemia effect is observed in the subject.

In another embodiment, a graft versus lymphoma effect is observed in the subject.

In another embodiment, a graft versus B cell neoplasm effect is observed in the subject.

In another embodiment, a graft versus myeloma effect is observed in the subject.

In another embodiment, one or more of graft versus tumor effect, graft versus leukemia effect, graft versus lymphoma effect, graft versus B cell neoplasm and graft versus myeloma effect is observed in the subject.

The invention also provides for a method of preventing GVHD in a subject that has received a transplant comprising administering a helminthic parasite preparation to the subject after the transplant wherein following the administration there is no decrease in the number of recipient regulatory T cells that express latency associated protein (LAP) after the transplant, thereby preventing GVHD.

In another embodiment, administration of the parasite preparation is prior to the onset of GVHD.

In another embodiment, the parasite preparation is administered daily, weekly, bi-weekly or every two weeks after the transplant or wherein the parasite preparation is administered in decreasing intervals of time following the transplant.

In another embodiment, no increase in the level of IFNγ and/or TNFα in the serum of the subject following administration of the parasite preparation as compared to the level before administration, indicates prevention of GVHD.

In another embodiment, GVHD is prevented if, following administration, the subject does not have an onset of one or more of a symptom of GVHD selected from the group consisting of: skin rash, diarrhea, liver disease, weight loss/anorexia, nausea, and vomiting.

In another embodiment, GHVD is prevented if following administration there is no increase in the level of IFNγ in the serum of the subject.

In another embodiment, GVHD is prevented if following administration of a helminthic parasite preparation there is no increase in the level of IFNγ in the serum of the subject and no onset of a symptom of GVHD selected from the group consisting of: skin rash, diarrhea, liver disease, weight loss/anorexia, nausea, and vomiting.

In another embodiment, GVHD is treated if following administration of a helminthic parasite preparation, there are no detectable apoptotic bodies in tissue derived from the upper gastrointestinal tract.

In another embodiment, the level of IFNγ and/or TNFα in the serum of the subject is measured prior to administration of the parasite preparation and after administration.

In another embodiment, no change in number of latency associated protein (LAP) expressing recipient regulatory T cells of the subject following administration of the parasite preparation as compared to the level before administration, indicates prevention of GVHD.

In another embodiment, the number of LAP expressing recipient regulatory T cells of the subject is measured prior to administration of the parasite preparation and after administration.

In another embodiment, administration is continued for at least 6 months after transplant.

The invention also provides for a method of preventing GVHD in a subject prior to transplantation comprising: administering a helminthic parasite preparation to a subject prior to the transplant; wherein prevention of GVHD is indicated if the level of IFNγ and/or TNFα in the serum of the subject following the transplant as compared to the level before the transplant does not increase.

The invention also provides for a method of preventing GVHD in a subject prior to transplantation comprising: administering a helminthic parasite preparation to a subject prior to the transplant; wherein prevention of GVHD is indicated if the number of recipient regulatory T cells expressing latency associated protein (LAP) does not decrease following the transplant.

In another embodiment, GVHD is prevented if following administration the subject does not have an onset of one or more of a symptom of GVHD selected from the group consisting of: skin rash, diarrhea, liver disease, weight loss/anorexia, nausea, and vomiting.

In another embodiment, GHVD is treated if following administration there is no increase in the level of IFNγ in the serum of the subject.

In another embodiment, GVHD is prevented if following administration of a helminthic parasite preparation there is no increase in the level of IFNγ in the serum of the subject and no onset of a symptom of GVHD selected from the group consisting of: skin rash, diarrhea, liver disease, weight loss/anorexia, nausea, and vomiting.

In another embodiment, GVHD is treated if following administration of a helminthic parasite preparation, there are no detectable apoptotic bodies in tissue derived from the upper gastrointestinal tract.

In another embodiment, the parasite preparation is administered eight weeks or less prior to the transplant.

In another embodiment, the transplant is a bone marrow transplant.

In another embodiment, the parasite preparation comprises 500-7500 parasites.

In another embodiment, the parasite preparation is administered orally.

In another embodiment, the parasite preparation is administered in combination with a second agent. As used herein, a second agent includes but is not limited to an immunosuppressant, for example a glucocorticoid. A second agent also includes a steroid, for example, prednisone, cyclosporine and azathioprine.

In another embodiment, the Helminth is selected from the group consisting of: helminths that colonize humans; and helminths that colonize non-human mammals.

The invention also provides for a method of monitoring the treatment efficacy of a parasite preparation for GVHD in a subject following a transplant, comprising: administering a helminthic parasite preparation to a subject with GVHD; and determining the level of production of IFNγ and/or TNFα by donor regulatory T-cells isolated from the subject following the transplant, and/or the level of IFNγ and/or TNFα in the serum of the subject, wherein a decrease in the level of production of IFNγ and/or TNFα by donor regulatory T-cells, and/or a decrease in the level of IFNγ and/or TNFα in the serum of the subject after administration of the parasite preparation as compared to before administration indicates the treatment efficacy.

The invention also provides for a method of monitoring the treatment efficacy of a parasite preparation for GVHD in a subject following a transplant comprising: administering a helminthic parasite preparation to the subject; and determining the number of latency associated protein (LAP) expressing donor regulatory T cells isolated from the subject after the transplant and/or LAP expressing recipient regulatory T cells; wherein an increase in number of LAP expressing donor and/or recipient T cells after administration of the parasite preparation as compared to before administration indicates the treatment efficacy.

In another embodiment, the transplant is a bone marrow transplant.

In another embodiment, GVHD is acute or chronic.

The invention also provides for a method of identifying a parasite preparation that treats or prevents GVHD in a subject prior to or after a transplant.

BRIEF DESCRIPTION OF THE DRAWINGS

FIGS. 2A-2H demonstrate that Helminth infection is associated with decreased GVHD-related inflammatory changes in the colon and the lungs (colons from control (A and B and lung (C)) and helminth-infected (D and E) mice low (10×) (A and D) and high (40×) (B and E) power of magnification and helminth-infected lung at 20× magnification (F); statistical analysis (G) of colon tissues from 10 uninfected control and 10 *H. bakeri* (polygyrus)-infected mice from 3 independent experiments; and statistical analysis (H) of GVHD-related inflammation in the lung from 6 uninfected control and 6 *H. bakeri* (polygyrus)-infected mice from 2 independent experiments).

FIGS. 3A-3F demonstrate that Helminths do not interfere with the expansion of donor T cell graft and promote the survival of recipient T cells. Splenic (upper row) and MLN (lower row) CD3+ T cells isolated 6 days after BMT from *H. bakeri* (polygyrus)-infected mice (right) (B) and from uninfected control recipients with GVHD (left) (A). The percentage of cells in the corresponding quadrants is shown. Representative example from multiple experiments. Splenic (upper row) and MLN CD3+ T cells (lower row) isolated 6 days after BMT from *H. bakeri* (polygyrus)-infected mice (right) (D) and from uninfected control recipients with GVHD (left) (C). The percentage of cells in the corresponding quadrants is shown. Representative example from multiple experiments. Statistical analysis of the percentage of splenic (left) (E) and MLN (right) (F) recipient T cells with N representing the number of mice utilized cumulatively in multiple experiments.

FIGS. 11A-11F present data demonstrating that no GVHD-related changes were evident in *H. bakeri*-infected or control mice that underwent T cell depleted bone marrow (TCD BM) transfer (weight change in helminth-infected (open squares) and uninfected (closed squares) mice after TCD BM transfer (A); disease score of uninfected control (closed squares) and *H. bakeri*-infected mice (open squares) (B); colons (C) and lungs (E) from control and colons (D) and lungs (F) from helminth-infected (B, right) mice).

FIG. 14 demonstrates that CD4+ CD25+ cells are enriched for FoxP3+ Tregs. Magnetically separated CD25 positive and CD25 negative splenic CD4 T cells from mice with no BMT were stained for FoxP3 and CD4.

FIGS. 15A-15D demonstrate that Helminths do not interfere with GVT. TCD BM transferred uninfected (A) or helminth-infected (B) mice displayed significant tumor activity while no tumor was evident in helminth-infected mice that survived GVHD (C) (TCD BM+SpI T cells (*H. bakeri*)). (D) Kaplan Meier analysis showing helminthic protection from GVHD and tumor challenge ($p<0.05$ between TCD BM+ T cells (*H. bakeri*) and other groups.

DETAILED DESCRIPTION OF THE INVENTION

Figure 1A:
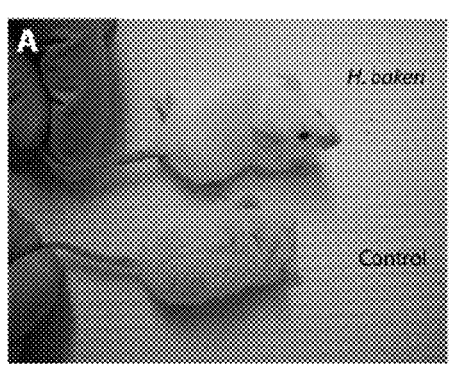
FIGS. 1A-1D demonstrate that Helminths regulate acute GVHD in mice. (A) *Heligmosomoides bakeri* (polygyrus) infection protects mice from the severe inflammation during acute GVHD. (B) Kaplan Meier survival curves of *H. bakeri* (polygyrus)-infected (open squares) or uninfected (closed squares) Balb/C recipients transferred TCD-BM and total splenic T cells from C57BL/6 mice. Cumulative data from three independent experiments with 9 animals in control and 10 mice in the *H. bakeri* group (p<0.0001). (C) The weight change in these mice during the entire follow-up of the survival experiment (p=not significant (NS)). (D) The disease score between the control (N=9) and *H. bakeri*-infected mice (N=10) over the entire course of the survival experiment (p<0.005).

As used herein, "Graft Versus Host Disease" (GVHD) means a complication that can occur after a non-autologous transplant, for example a stem cell or bone marrow transplant, wherein transplanted donor cells attack the transplant recipient. Acute GVHD is mediated by allo-reactivity of donor T lymphocytes to recipient major or minor histocompatibility antigens. GVHD is not an auto-immune disease, process or reaction. GVHD is characterized by symptoms including but not limited to skin rash, diarrhea, liver disease, weight loss/anorexia and nausea.

As used herein, "acute GVHD" means GVHD that occurs within the first 100 days after transplantation. "Acute GVHD" is characterized by damage to the skin, liver and the gastrointestinal tract. Common symptoms of acute GVHD include but are not limited to a skin rash, abdominal pain or cramping, nausea, vomiting and diarrhea, dry or irritated eyes and jaundice.

As used herein "chronic GVHD" means GVHD that occurs after day 100 post-transplantation. "Chronic GVHD" exhibits multi-organ infiltration similar to various autoimmune diseases. Common symptoms of chronic GVHD include but are not limited to a skin rash with raised, discolored areas, as well as skin tightening or thickening dry eyes or vision changes, dry mouth, white patches inside the mouth and sensitivity to spicy foods, fatigue, muscle weakness, chronic pain, shortness of breath, vaginal dryness and weight loss.

As used herein, "graft versus tumor effect" (GVT) means elimination of malignant tumors following transplantation. GVT occurs, for example, after allogeneic bone marrow or stem cell transplantation.

As used herein, "graft versus leukemia effect" (GVL) means elimination of leukemia cells following transplantation. GVT occurs, for example, after allogeneic bone marrow or stem cell transplantation.

As used herein, "graft versus lymphoma effect" means elimination of lymphoma cells following transplantation.

As used herein, "graft versus B cell neoplasm" effect" (GVL) means elimination of cells of a B cell neoplasm, for example, myeloma.

Symptoms of, and diagnostic methods for GVHD are described below in the section entitled "GVHD".

As used herein "transplant" means an allogeneic/non-autologous or syngeneic bone marrow or stem cell transplant. As used herein, "transplant" also refers to transplantation of any allogeneic/non-autologous or syngeneic tissue, organ or cell.

As used herein, "allogeneic transplant", "allotransplant" or "non-autologous/non-syngeneic transplant" means the transplantation of cells, tissues or organs to a recipient from a genetically non-identical donor of the same species.

As used herein, the term "parasite preparation" or "helminth parasite preparation" includes, but is not limited to, any one of whole parasite, parasite extract, parasite ova, parasite ova extract, parasite egg, parasite egg extract, parasite larvae, parasite larvae extract, parasite cercariae and parasite cercariae extract. A "parasite preparation" may also be an isolated protein, polynucleotide carbohydrate or lipid derived from the parasite and its extract.

As used herein, "patient" or "subject" refers to a mammal that has had a transplant or is a candidate for, a transplant. For example, a medical professional may determine that a subject will benefit from a transplant. "Patient" or "subject" also refers to a subject diagnosed with GVHD.

The term "patient" or "subject" includes human and other mammalian subjects that receive either prophylactic or therapeutic treatment.

As used herein, "mammal" refers to any mammal, preferably a human, but also including, for example, mouse, rat, sheep, monkey, goat, rabbit, hamster, horse, cow or pig.

A "non-human mammal", as used herein, refers to any mammal that is not a human.

As used herein, "treating GVHD" means alleviating or ameliorating one or more symptoms of GVHD. A subject wherein the severity of the disease is reduced to a lesser grade, as defined herein in the section entitled "GVHD", is treated.

As used herein, "preventing GVHD" in a subject means that the subject is treated at a time when the subject exhibits no detectable symptom of GVHD used to determine the stage or grade of the disease as described herein below in the section entitled "GVHD".

Success of treatment or prevention of GVHD is determined by invasive and non-invasive methods, such as staging a skin rash by non-invasive observation of the skin of a subject, and/or by histopathology of a tissue sample obtained by biopsy, staging the involvement of the gut (e.g., by imaging studies laboratory studies, and staging liver involvement, for example by analysis of liver function tests).

"Treatment", or "treating" as it refers to GVHD, is defined as the application or administration of a parasite preparation to a subject or patient who has GVHD, with the purpose to cure, heal, alleviate, relieve, alter, remedy, ameliorate, improve or affect the GVHD, or symptoms of GVHD. The term "treatment" or "treating" is also used herein in the context of administering a parasite preparation prophylactically.

The term "effective dose" or "effective amount" or "effective dosage" or "therapeutic dosage" is defined as an amount sufficient to achieve complete or at least partial resolution of the symptoms of GVHD. The terms "therapeutically effective dose" and "therapeutically effective amount" are defined as an amount sufficient to completely or at least partially arrest GVHD and its complications in a patient already suffering from GVHD. As used herein, "treating" GVHD refers to preventing the onset of GVHD and/or reducing, delaying, or eliminating one or more symptoms of GVHD as discussed herein. By "treating" is meant restoring the patient or subject to the basal state as defined herein, and/or to prevent GVHD in a subject at risk thereof. Alternatively, "treating" means arresting or otherwise ameliorating symptoms of a disease.

As used herein, "basal state" refers to a state with no detectable symptoms of GVHD. "Basal state" also means that the subject remains without detectable symptoms of GVHD, for example, no onset of a skin rash, diarrhea and/or weight loss or anorexia when treated prophylactically. As used herein, "modulate" or "modulation" refers to a change (increase or decrease) in any one of the level of production of IFN$\gamma$ and/or TNF$\alpha$ by donor T cells isolated from a subject following a transplant, the level of IFN$\gamma$, or TNF$\alpha$ in the serum of a subject following a transplant, or the number of recipient T cells or donor T cells isolated from a subject following a transplant that express latency associate protein (LAP).

As used herein, "decrease" means 1, 2, 3, 4, 5, 10, 15, 20, 25, 30, 35, 40, 45, 50, 100, 500, 1000 or 10,000-fold less after administration of a parasite preparation of the invention as compared to before administration of a parasite preparation of the invention.

As used herein, "decrease" means the level of IFN$\gamma$ and/or TNF$\alpha$ in the serum is 1, 2, 3, 4, 5, 10, 15, 20, 25, 30, 35, 40, 45, 50, 100, 500, 1000 or 10,000-fold less after administration of a parasite preparation of the invention as compared to before administration of a parasite preparation of the invention.

As used herein, "decrease" means the level the production of IFN$\gamma$ and/or TNF$\alpha$ by donor T cells is 1, 2, 3, 4, 5, 10, 15, 20, 25, 30, 35, 40, 45, 50, 100, 500, 1000 or 10,000-fold less after administration of a parasite preparation of the invention as compared to before administration of a parasite preparation of the invention.

As used herein, "decrease" also means 1, 5, 10, 15, 20, 25, 30, 35, 40, 45, 50, 55, 60, 65, 70, 75, 80, 85, 90, 95, 99 or 100% less after administration of a parasite preparation of the invention as compared to before administration of a parasite preparation of the invention.

As used herein, "decrease" also means the level of IFN$\gamma$ and/or TNF$\alpha$ in the serum of the transplant recipient is 1, 5, 10, 15, 20, 25, 30, 35, 40, 45, 50, 55, 60, 65, 70, 75, 80, 85, 90, 95, 99 or 100% less after administration of a parasite preparation of the invention as compared to before administration of a parasite preparation of the invention.

As used herein, "decrease" also means the level the production of IFN$\gamma$ and/or TNF$\beta$ by donor T cells 1, 5, 10, 15, 20, 25, 30, 35, 40, 45, 50, 55, 60, 65, 70, 75, 80, 85, 90, 95, 99 or 100% less after administration of a parasite preparation of the invention as compared to before administration of a parasite preparation of the invention.

As used herein, "increase" means 1, 2, 3, 4, 5, 10, 15, 20, 25, 30, 35, 40, 45, 50, 100, 500, 1000 or 10,000-fold more after administration of a parasite preparation of the invention as compared to before administration of a parasite preparation of the invention.

As used herein, "increase" also means that the number and/or percent of FoxP3+ donor and/or recipient derived regulatory T cells in a subject following a transplant is 1, 2, 3, 4, 5, 10, 15, 20, 25, 30, 35, 40, 45, 50, 100, 500, 1000 or 10,000-fold more after administration of a parasite preparation of the invention as compared to before administration of a parasite preparation of the invention.

As used herein, "increase" also means that the number and/or percent of FoxP3+ donor and/or recipient derived regulatory T cells in a subject following a transplant is 1, 5, 10, 15, 20, 25, 30, 35, 40, 45, 50, 55, 60, 65, 70, 75, 80, 85, 90, 95, 99 or 100% more after administration of a parasite preparation of the invention as compared to before administration of a parasite preparation of the invention.

As used herein "monitoring the treatment" means determining whether, following treatment of a subject diagnosed with GVHD, the subject has been treated such that the symptoms of GVHD are either arrested or ameliorated and/or GVHD and/or its attendant symptoms are alleviated or abated.

As used herein, "control subject" means a subject that has not been diagnosed with GVHD and/or does not exhibit any detectable symptoms associated with GVHD.

As used herein, the term "specific-pathogen free" as applied to animals raised for use in the present invention means the animals are known to be free of a specific pathogenic microorganism that can cause disease in a target animal or human. Methods for raising pathogen free animals are known in the art, e.g., see references complied by Brown et al., A Bibliography on the Culture and Maintenance Specific Pathogen-Free Organisms, available at http://www.ctsa.org/upload/publication/CTSA.sub.—116631681202959092495.pdf (hereby incorporated by reference). Brown et al. provides references for raising farm and laboratory animals in an SPF environment, as well as procedures and requirements on building design and management. Also see M. Michael Swindle (J. Invest. Surg., 9:267-271, 1996, hereby incorporated by reference) for SPF procedure and disclosure of several potential human viral and bacterial pathogens of concern.

As used herein, the term "regulatory T cells" refers to a lymphocyte cell population which secretes at least 2-fold (e.g., 3-fold, 4-fold, 5-fold, 6-fold, 8-fold, 10-fold or more) more IL-10 and/or TGF$\beta$, as compared to naive T cells. Methods of determining IL-10 or TGF$\beta$ secretion are well established. For example, cytokine secretion may be determined by culturing cells in vitro for 24 or 48 hours with or without a T cell stimulant, for example, anti-CD3, and then assaying the culture supernatant for a cytokine of interest using cytokine specific ELISA. In addition, regulatory T cells are characterized by a high level of FoxP3 transcript as compared to other types of T cells (e.g., naive T cells). By "high level of FoxP3 transcript," is meant at least a 4-fold increase in the level as compared to other types of T cells.

FoxP3 is detected by using real-time PCR or quantitative PCR (e.g., using PCR primers CCCAGGAAAGACAG-CAACCTT (SEQ ID NO:1), TTCTCACAACCAGGC-CACTTG (SEQ ID NO:2), and labeled probe 6FAM-ATC-CTACCCACTGCTGGCAAATGGAGT-C-TAMRA (SEQ ID NO:3) as described in Hori, S., T. Nomura, and S. Sakaguchi. 2003. Control of regulatory T cell development by the transcription factor Foxp3. Science. 299:1057-1061). Values are normalized to HPRT expression, a housekeeping gene. Alternatively, FoxP3 protein product, Scurfin, can be detected by Western blotting analysis as known in the art, e.g., using Goat Anti-FoxP 3 (FoxP3) Polyclonal Antibody (Catalog Number ab248 1, Novus Biologicals, Littleton, Colo.). Regulatory T cells may also produce significantly less IFNγ as compared to other T cells (e.g., naive T cells), i.e., at least 2-fold, preferably 3-fold, 4-fold, 5-fold, 6-fold, 7-fold, 8-fold, 10-fold or less. Regulatory T cells can be detected by using intra-cytoplasmic flow analysis to detect T cells expressing IL10 and/or TGFβ and low levels of or no detectable IFNγ.

Additional optional markers as described herein below may also be used for detecting regulatory T cells or the activity of regulatory T cells. Internal markers useful for determining regulatory T cell activity include but are not limited to transcription factors, for example, Scurfin, Smad7, Gata3 and Tbet (Tbx21). Cell surface markers useful for determining regulatory T cell activity include but are not limited to CD4, CD45RB$^{lo}$, CD45Rc, Cytolytic T lymphocyte associated antigen 4 (CTLA-4), Ox40, 4-1BB, CD25, CD103, CD62L, αβintegrin, latency-associated peptide (LAP) or glucocorticoid induced TNF receptor family related protein (GITR), chemokine receptor CCR5 and TI-ST2 Secreted markers useful for determining regulatory T cell activity include but are not limited to IL4, ILI 3, IL-5, IL-10 or TGFβ and PgE2.

The activity of regulatory T cell may be measured by monitoring the level of a regulatory T cell internal marker (e.g., a transcription factor such as FoxP3 mRNA or its protein product Scurfin, Smad7, Gata3, or Tbet (Tbx21)), or a regulatory T cell surface marker (e.g., CD4, CD45RB$^{lo}$, CD45Rc, Cytolytic T lymphocyte associated antigen 4 (CTLA-4), Ox40, 4-1BB, CD25, CD103, CD62L, αβintegrin, latency-associated peptide (LAP) or glucocorticoid induced TNF receptor family related protein (GITR), As used herein, "naive T cells" means T-cells arising from the immune system's production of fresh cells in the bone marrow. Naive T-cells respond to newly encountered pathogens containing antigens the immune system has not yet processed. The naive T-cells may be identified according to methods known in the art (for reviews, see, e.g., Tough et al., 1999, Immunol Rev. 170:39-47; Itano et al., 2003, Nat Immunol. 4(8):733-9; Berard et al., 2002, Immunology. 106(2):127-38).

As used herein, the term "the level of a regulatory T cell marker" refers to the amount of a specific regulatory T cell marker in a target, e.g., measured by micrograms or molar amounts. Typically, the regulatory T cell marker is a protein, for which the amount may be measured by any known methods in the art for protein quantitation, for example, by ELISA, western blot, immunoprecipitation, radioimmunoassay, or FACS analysis (e.g., in Innis et al., (1990) Academic Press, Inc.; Molecular Cloning, A Laboratory Manual (2d Edition, Sambrook, et al. (1989); and Current Protocols in Molecular Biology (1997, Ausubel et al., John Wiley & Sons, Inc.). The level of a protein marker may also be measured at its mRNA level according to methods known in the art, e.g., by northern blot, quantitative RT-PCR, microarray analysis (e.g., in Innis et al., (1990) Academic Press, Inc.; Molecular Cloning, A Laboratory Manual (2d Edition, Sambrook, et al. (1989); and Current Protocols in Molecular Biology (1997, Ausubel et al., John Wiley & Sons, Inc.).

As used herein, the term "parasite preparation that alters a regulatory T cell activity" refers to a parasite preparation which changes the activity of a regulatory T cell in a target by at least 40%, e.g., 50%, 80%, 100%, 2 fold, 4 fold, 6 fold, 8 fold, 10 fold, or more upon contacting the target, compared to the regulatory T cell activity in the target in the absence of the parasite preparation. Regulatory T cell activity includes any in vivo activity characterized by a decrease in symptoms of disease or signs of inflammation, for example, reduced inflammation as determined by histological analysis of for example, a tissue sample from the skin, GI system or liver, a reduction in the level of inflammatory cytokines in the serum and a reduction in the level of activity of one or more of effector B cell, T cell, monocyte, macrophage or dendritic cell.

As used herein, the term "treatment efficacy" refers to the effectiveness of a treatment of a disease using a parasite preparation. "Treatment efficacy" is usually measured by the clinical response to a specific disease, for example, GVHD, for which the animal has been or is being treated with a parasite preparation.

As used herein, the term "disease caused by an altered immune response" refers to a disease which an animal (e.g., a human) develops due to a difference in its immune response compared to a non-disease animal. For example, the disease animal may have an abnormal (e.g., excessive or non-sufficient) immune response to an antigen (e.g., a self or a non-self antigen) compared to a response to the same antigen in a normal non-disease animal. A "disease caused by an altered immune response", according to the present invention, includes, but is not limited to, a Th1 related disease or a Th2 related disease as described herein.

As used herein, the term "Th1 related disease" refers to a disease in which Th1 cells support, cause or mediate the disease process or in which Th1 cells are involved in curing or alleviating the symptoms of the disease, which may be represented by an enhanced or reduced Th1 activity. By "enhanced", it is meant that a diseased animal has an increase (e.g., at least 2-fold, and possible 5-fold, 6 fold, 8 fold, 10-fold, or more) in its Th1 activity, compared to another animal without the disease. An enhanced Th1 activity may be measured by an increase in the level of secreted cytokines (e.g., IL-2, IFNγ., TNFα, IgG2a, IL-12, IL-18, IL-23), or a decrease in the level of secreted cytokines (e.g., IL-4, IL-13), according to methods known in the art. By "reduced", it is meant that a diseased animal has a decrease (e.g., at least 50% lower, or 2 fold, and possible 5-fold, 6 fold, 8 fold, 10-fold, or lower) in its Th1 activity, compared to another animal without the disease. A reduced Th1 activity may be measured by a decrease in the level of secreted cytokines (e.g., IFNγ, TNFα, IgG2a), or an increase in the level of secreted cytokines (e.g., IL-4, IL-13), according to methods known in the art, and as described herein and in U.S. applications with Ser. Nos. 09/209,732 and 09/362, 598, the entirety of each is incorporated by reference.

As used herein, the term "reduced" is used interchangeably with the term "decreased", and the term "increased" is used interchangeably with the term "enhanced."

As used herein, the term "Th2 related disease" refers to any disease, in which Th2 cells support, cause or mediate the disease process or in which Th2 cells are involved in curing or alleviating the symptoms of the diseases, which may be represented by an enhanced or reduced Th2 activity. By "enhanced", it is meant that a diseased n animal has an increase (e.g., at least 2-fold, and possible 5-fold, 6 fold, 8 fold, 10-fold, or more) in its Th2 activity, compared to another animal without the disease. An enhanced Th2 activity may be measured by an increase in the level of secreted cytokines and antibodies (e.g., IL-4, IL-5, IgE and IgG1) according to methods known in the art. By "reduced", it is meant that a diseased animal has a decrease (e.g., at least 50%, 2-fold, and possible 5-fold, 6 fold, 8 fold, 10-fold, or lower) in its Th2 response, compared to another animal without the disease. A reduced Th2 activity may be measured by a decrease in the level of secreted cytokines and antibodies (e.g., IL-4, IL-5, IgE and IgG1) according to methods known in the art, and as described herein and in U.S. applications with Ser. Nos. 09/209,732 and 09/362,598, the entirety of each is incorporated by reference.

Helminthic Parasites Useful According to the Invention

Useful helminthic parasites include, but are not limited to, two groups. The first group is helminthic parasites that naturally colonize humans and the second group is helminthic parasites that colonize non-human mammals, for example, mouse, rat, cat, dog, pig, but may afford protection to humans.

In the first group, helminthic parasites are elaborate multicellular worms with complex life cycles and development. The nematodes (non-segmented round worms), and the platyhelminths (flat worms) are two groups of helminths that colonize the human intestines. In accordance with the present invention, any one of a number of helminth parasites that naturally colonize humans or animals will provide the intended results.

Nematodes that frequently inhabit the human gut are *Ascaris lumbricoides*, *Enterobius vermicularis* (pin worm), *Trichuris trichiura* (whipworm), *Ancylostoma duodenale* and *Necator americanus* (hookworms), and *Strongyloides stercoralis*. *Trichinella spiralis* infests the small intestine briefly.

The platyhelminths include the trematodes and cestodes. The most common adult trematodes that reside in the human intestines are *Fasciolopsis*, *Echinostoma* and *Heterophyes* species. Those that live in the biliary system include *Clonorchis sinensis*, *Opisthorchis viverrini* and *felineus*, and *Fasciola hepatica*. *Schistosoma* dwell in the venous system, but several species chronically affect the gut by the passage of eggs through the intestinal wall. Adult cestodes commonly infecting humans are *Diphyllobothrium* species (fish tapeworm), *Taenia saginata* (beef tapeworm), *Taenia solium* (pork tapeworm) and *Hymenolepsis nana* (dwarf tapeworm).

Other helminths of interest include the filarial parasites and the lung flukes. These do not have a gut phase, but stimulate strong Th2-type responses.

The second general group of helminthic parasites that can be utilized in the present invention include helminths that colonize animals, but may afford humans protection against immune-mediated diseases. These include *Trichuris muris* (mouse whipworm), *Trichinella spiralis*, *Nippostrongylus brasiliensis*, *Heligmonsomoides polygyrus* and *Hymenolepsis nana*, all of which are intestinal helminths that infect mice. Additionally, *Angiostrongylus* is a rat helminth. *Trichuris suis* and *Ascaris suum* are pig helminths that can infect humans. *Trichuris vulpis*, *Toxocara* species, *Gnathostoma*, and *Ancylostoma* are dog or cat helminths that also can infect humans. *Anisakis* and *Pseudoterranova* are nematodes of marine mammals that can transmit to humans. Bird schistosomes can transiently infect humans. Such schistosomes include *S. douthitti*, *Trichobilharzia ocellata*, *T. stagnicolae*, *T. physellae*, and *Gigantobilharzia huronensis*.

The helminthic preparation may be selected from the group consisting of helminiths that naturally colonize humans and helminths that colonize animals but may protect humans or animals from a disease caused by an altered immune response.

In some embodiments of the invention, the helminth parasite is a nematode, and may be selected from the group such as *Ascaris lumbricoides*, *Enterobius vermicularis*, *Trichuris trichiura*, *Ancylostoma duodenale* and *Necator americanus*, *Strongyloides stercoralis* and *Trichinella spiralis*.

In other embodiments of the invention, the helminthic parasite is a platyhelminth, and may be selected from the group consisting of trematodes and cestodes, such as *Fasciolopsis*, *Echinostoma* and *Heterophyes* species, *Clonorchis sinensis*, *Opisthorchis viverrini*, *Opisthorchis felineus*, *Fasciola hepatica*, *Schistosoma* species, *Diphyllobothrium* species, *Taenia saginata*, *Taenia solium* and *Hymenolepsis nana*.

In other embodiments, the helminthic parasite is selected from the group consisting of filarial parasites and lung flukes.

In preferred embodiments, the helminthic parasites are selected from the group consisting of *Trichuris muris*, *Trichinella spiralis*, *Nippostrongylus prasiliensis*, *Heligmonsomoides polygyrus*, *Hymenolepsis nanan*, *Angiostrongylus* species, *Trichuris suis*, *Ascaris suum*, *Trichuris vulpis*, *Toxocara* species, *Gnathostoma* species, *Ancylostoma* species, *Anisakis* species and *Pseudoterranova* species.

It is preferred that the preparatory animals for parasite production and preparation are raised in specific pathogen-free (SPF) (e.g., specific human pathogen free) environment.

Symptoms of GVHD

The primary symptoms of Acute GVHD include but are not limited to an erythematous maculo-papular rash that can mimic epidermolytic skin lesions such as seen with Stevens Johnson syndrome; diarrhea, more seldom with abdominal pain, nausea and vomiting and/or anorexia The skin disease associated with acute GVHD is clinically staged as follows:
 Stage 1—Maculopapular rash over <25 percent of body area;
 Stage 2—Maculopapular rash over 25 to 50 percent of body area;
 Stage 3—Generalized erythroderma;
 Stage 4—Generalized erythroderma with bullous formation, often with desquamation.

Skin disease diagnosis is established after drug related skin eruptions, viral disease and radiation dermatitis are ruled out.

In certain instances, subjects diagnosed with acute GVHD have oral lesions, for example, erythema, erosions, ulcers, lichenoid lesions, and xerostomia, and pain. A skin biopsy may not be necessary for diagnosis of GVHD if GVHD is suggested by the manifestation of symptoms in other organ systems. However, in patients with only skin involvement/symptoms, a skin biopsy is recommended.

Skin biopsy findings are never pathognomonic, but are indicative of acute GVHD and can include: interface dermatitis (vacuolization of the basal layer of the epidermis and a lymphocytic infiltrate in the superficial dermis) and epidermal apoptotic keratinocytes with IgM and complement deposition at the basement membrane as demonstrated by immunofluorescence.

Histo-pathological grading of skin disease associated with GVHD is as follows:
 Grade 0—normal skin or changes not referable to GVHD;
 Grade 1—vacuolization of the basal layer at the dermal-epidermal junction;
 Grade 2—Basal layer vacuolization, necrotic epidermal cells, lymphocytic infiltrate;
 Grade 3—Grade 2 changes plus cleft formation at the dermal-epidermal junction;
 Grade 4—Grade 2 changes plus separation of the epidermis from the dermis The diagnosis of gastrointestinal (GI) GVHD typically requires tissue diagnosis via a biopsy, with apoptotic bodies being consistent withf GVHD. Usually a colonoscopy is indicated in patients with diarrhea. In patients with nausea and vomiting an EGD esophagogastroduodenoscopy) is indicated.

Clinical staging of GI disease is as follows:
Stage 1—Diarrhea 500 to 1000 mL/day
Stage 2—Diarrhea 1000 to 1500 mL/day
Stage 3—Diarrhea 1500 to 2000 mL/day
Stage 4—Diarrhea >2000 mL/day OR pain OR ileus A diagnosis of GI GVHD requires first ruling out *Clostridium difficile* or CMV or other infections.

Acute GVHD is also diagnosed by identifying a subject as having liver disease indicated by the following laboratory findings:
increased bilirubin increase
increased aspartase aminotransferase (AST)/alanine transaminase (ALT)
increased alkaline phosphatase; and/or histopathological findings including bile duct damage.

Liver disease is clinically staged as follows:
Stage 1—Bilirubin 2 to 3 mg/dL
Stage 2—Bilirubin 3 to 6 mg/dL
Stage 3—Bilirubin 6 to 15 mg/dL
Stage 4—Bilirubin >15 mg/dL Assessment of the stage of liver involvement is considered in combination with information regarding the stage of cutaneous and gastrointestinal tract involvement to determine the overall severity grade of acute GVHD. (See 'Grading' below)

As described above, the overall grade of clinical GVHD activity is as follows:
Grade A—Stage 1 skin involvement alone (maculopapular rash over <25 percent of the body) with no liver or gastrointestinal involvement
Grade B—Stage 2 skin involvement; Stage 1 to 2 gut or liver involvement
Grade C—Stage 3 involvement of any organ system (generalized erythroderma; bilirubin 6.1 to 15.0 mg/dL; diarrhea 1500 to 2000 mL/day)
Grade D—Stage 4 involvement of any organ system (generalized erythroderma with bullous formation; bilirubin >15 mg/dL; diarrhea >2000 mL/day OR pain OR ileus).

The severity of GVHD can be determined by grading the disease state according to one or more of the following severity indices used by health care providers.

Acute GVHD severity can be graded (grades 0-1V) by the pattern of organ involvement using the classic Glucksburg-Seattle criteria (GSC).

Glucksberg Grading is as follows:
I Stage 1 or 2 skin involvement; no liver or gut involvement; Eastern Cooperative Oncology Group Performance Status (ECOG PS 0);
II Stage 1 to 3 skin involvement; Grade 1 liver or gut involvement; ECOG PS1;
III Stage 2 or 3 skin, liver or gut involvement; ECOG PS 2;
IV Stage 1 to 4 skin involvement; Stage 2 to 4 liver or gut involvement; ECOG PS 3.

The International Bone Marrow Transplant Registry (IBMTR) has developed a Severity Index by regrouping the patterns of organ involvement into five Indexes (0-D) that appeared more predictive of transplant-related mortality (TRM) and transplant failure (TF, relapse or TRM). This index is based on the results of an analysis of the severity of GVHD involvement in the skin, liver, and gut.

International Bone Marrow Transplant Registry Severity Index
Stage 1 skin involvement; no liver or gut involvement
B-Stage 2 skin involvement; no liver or gut involvement
C-Stage 3 skin involvement; stage 1 to 2 gut or liver involvement
D-Stage 4 skin, liver or gut involvement Organ Stage Description is as follows:
Skin
Stage 1 Maculopapular rash over <25% of body area
Stage 2 Maculopapular rash over 25-50% of body area
Stage 3 Generalized erythroderma
Stage 4 Generalized erythroderma with bullous formation and often with desquamation
Liver
Stage 1 Bilirubin 2.0 to 3.0 mg/dL; SGOT 150 to 750 international units
Stage 2 Bilirubin 3.1 to 6.0 mg/dL
Stage 3 Bilirubin 6.1 to 15.0 mg/dL
Stage 4 Bilirubin >15.0 mg/dL
Gut
Stage 1 Diarrhea 30 mL/kg or 500 mL/day
Stage 1 Diarrhea 60 mL/kg or 1000 mL/day
Stage 3 Diarrhea 90 mL/kg or 1500 mL/day
Stage 4 Diarrhea 90 mL/kg or 2000 mL/day; or severe abdominal pain with or without ileus Detection of GVHD Symptoms GVHD symptoms can be detected by laboratory studies.

Laboratory study results in GVHD are as follows:
CBC—Autoimmune cytopenias (eg, thrombocytopenia, anemia, leukopenia) may be observed with chronic GVHD
Liver function tests—Elevation of the alkaline phosphatase concentration an early sign of liver involvement by GVHD; hypoalbuminemia is typically due to GVHD-associated intestinal protein leak and a negative nitrogen balance
Serum electrolytes and chemistries (eg, potassium, magnesium, bicarbonate levels) may be altered; massive diarrhea and diminished oral intake can lead to serious electrolyte abnormalities Other tests for detecting GVHD symptoms include:
Schirmer test—To measure the degree of tear formation by the lacrimal glands in chronic GVHD
Pulmonary function tests and arterial blood gas analysis—To identify obstructive pulmonary disease (eg, obliterative bronchiolitis) in chronic GVHD
Manometric studies of the esophagus in chronic GVHD.

Imaging studies useful for detecting GVHD symptoms include:
Hepatic and Doppler sonography
Barium swallow study
Skin punch biopsy
Upper GI endoscopy and biopsy in patients with persistent anorexia and vomiting
Flexible sigmoidoscopy or colonoscopy with biopsy of sigmoid or colonic lesions in patients with diarrhea
Liver biopsy (rarely done, usually only in patients with isolated hepatic findings)

Regulatory T Cells in Th1 or Th2 Related Diseases

Regulatory T cells can induce peripheral tolerance and limit mucosal reactivity (McGuirk P, Mills K H. Pathogen-specific regulatory T cells provoke a shift in the Th1/Th2 paradigm in immunity to infectious diseases. Trends Immunol 2002; 23(9):450-5). In various animal models, several regulatory T cell phenotypes have been reported. Regulatory T cells express various markers and have been indicated to involve in different diseases (See, e.g., Field, A. C., L. Caccavelli, M. F. Bloch, and B. Belton. 2003. Regulatory CD8+ T cells control neonatal tolerance to a Th2-mediated autoimmunity. Journal of Immunology. 170:2508-2515; von Herrath M G, Harrison L C. Antigen-induced regulatory T cells in autoimmunity. Nat Rev Immunol. March 2003; 3(3):223-32; Francois Bach J. Regulatory T cells under scrutiny. Nat Rev Immunol. March 2003; 3(3):189-98; Curotto de Lafaille M A, Lafaille J J. CD4(+) regulatory T cells in autoimmunity and allergy. Curr Opin Immunol. December 2002; 14(6):771-8; McGuirk P, Mills K H. Pathogen-specific regulatory T cells provoke a shift in the Th1/Th2 paradigm in immunity to infectious diseases. Trends Immunol. September 2002; 23(9):450-5; Tung K S, Agersborg S S, Alard P, Garza K M, Lou Y H. Regulatory T-cell, endogenous antigen and neonatal environment in the prevention and induction of autoimmune disease. Immunol Rev. August 2001; 182:135-48; Read S, Powrie F. CD4(+) regulatory T cells. Curr Opin Immunol. December 2001; 13(6):644-9; Yssel H, Lecart S, Pene J. Regulatory T cells and allergic asthma. Microbes Infect. September 2001; 3(11):899-904). In some systems, they are distinguished through differential expression of surface molecules like CD25 (Shevach, E. M. 2002. CD4+ CD25+ suppressor T cells: more questions than. answers. Nature Reviews Immunology. 2:389-400), CD45RB (Annacker, O. and F. Powrie. 2002. Homeostasis of intestinal immune regulation. Microbes & Infection. 4:567-574), and CTLA-4 (Read, S., V. Malmstrom, and F. Powrie. 2000. Cytotoxic T lymphocyte-associated antigen 4 plays an essential role in the function of CD25(+)CD4(+) regulatory cells that control intestinal inflammation. J. Exp. Med. 192:295-302). This pattern of cell surface protein expression suggests that they may be in a primed effector or memory state. These regulatory cells may mediate some of their affects through production of IL10 and TGFβ. Described is an anergic regulatory T cell (Tr1) that produces high levels of IL10 and TFGβ. Another cell called Th3 suppresses induction of experimental autoimmune encephalomyelitis primarily through production of TGFβ. Still others are not dependent on soluble IL10 or TGFβ, but instead express on their surface latency-associated peptide, which is the amino-terminal domain of the TGFβ. precursor peptide (Oida T, Zhang X, Goto M et al. CD4+CD25−T cells that express latency-associated peptide on the surface suppress CD4+ CD45RBhigh-induced colitis by a TGF-beta-dependent mechanism. J Immunol 2003; 170(5):2516-22). Internal cell markers have also been reported for regulatory T cells (Schubert L A, Jeffery E, Zhang Y, Ramsdell F, Ziegler S F, Scurfin (FOXP3) acts as a repressor of transcription and regulates T cell activation. J Biol Chem. Oct. 5, 2001; 276(40):37672-9). All references are hereby incorporated by references.

Rag mice reconstituted with CD4+, CD45$^{high}$ T cells can develop severe colitis, which can be prevented by co-transfer of CD4+, CD45$^{low}$ T cells (Annacker O, Powrie F. Homeostasis of intestinal immune regulation. Microbes & Infection 2002; 4(5):567-74). TGFβ and IL10 are required for protection suggesting a role for these cytokines in the regulatory process.

Helminthic Parasite Preparation According to the Invention

Helminths are parasitic animals (worms), which, depending on species, live in locations like the intestinal lumen, blood stream or muscles of the host. These organisms colonize more than ⅓ of the world population. Helminth colonization is most common in children living in warm climates and subject to poor sanitation. The infective forms of these organisms are spread through contact with contaminated soil, food or water. Before the 1940s, many children and adults in the United States carried helminths. Worm carriage was particularly common in rural areas of the South and in indigent populations of major cities (Elliott D E, Urban J F, Jr., Argo C K et al. Does the failure to acquire helminthic parasites predispose to Crohn's disease? FASEB J 2000; 14(12):1848-55). In the United States and Europe, helminthic colonization has steadily declined. They are found in recent immigrants from less developed countries (Salas S D, Heifetz R, Barrett-Connor E. Intestinal parasites in Central American immigrants in the United States. Arch Intern Med 1990; 150(7):1514-6) and in economically disadvantaged populations living in underserved regions of the United States like some Indian reservation (Healy G R, Gleason N N, Bokat R et al. Prevalence of ascariasis and amebiasis in Cherokee Indian school children. Public Health Rep 1969; 84(10):907-14). The prevalence of helminths is highest in warm climates and in populations subject to crowding, poor sanitation and impure food supply. Inflammatory bowel disease (IBD), rheumatoid arthritis and autoimmune diseases are rare in these same regions.

Nematodes that frequently inhabit the human gut are *Ascaris lumbricoides, Enterobius vermicularis* (pin worm), *Trichuris trichiura* (whipworm), *Ancylostoma duodenale* and *Necator americanus* (hookworms), and *Strongyloides stercoralis*. *Trichinella spiralis* infests the small intestine briefly.

The platyhelminths include the trematodes and cestodes. The most common adult trematodes that reside in the human intestines are *Fasciolopsis, Echinostoma* and *Heterophyes* species. Those that live in the biliary system include *Clonorchis sinensis, Opisthorchis viverrini* and *felineus*, and *Fasciola hepatica*. *Schistosoma* dwell in the venous system, but several species chronically affect the gut by the passage of eggs through the intestinal wall. Adult cestodes commonly infecting humans are *Diphyllobothrium* species (fish tapeworm), *Taenia saginata* (beef tapeworm), *Taenia solium* (pork tapeworm) and *Hymenolepsis nana* (dwarf tapeworm).

The host acquires various helminthic species through contact with soil, food or water contaminated with the infective form of the parasite. Children most frequently harbor helminthic infections because of their close contact with soil and suboptimal hygienic practices. Helminths incite an intestinal Th2 response, which can cause worm expulsion or limit the magnitude of infection. Most children living in non-industrialized countries have these parasites. Many helminthic species survive for years within the gut, biliary tree or mesenteric veins making thousands of eggs daily. Thus, beginning in childhood, these worms and/or their ova release molecules that bathe the intestinal mucosal surface for years inciting Th2-type inflammation.

A. Viable Organism Vaccines:

Viable helminthic parasite organisms may provide the most profound mucosal conditioning because of their relative longevity as compared to component vaccines. Viable organisms can be administered in either egg, larval, cercarial, or encysted larval forms depending on the helminth. Helminths that can colonize humans and a preparatory animal may be utilized.

The preparatory animal may need manipulation to allow high patency by the helminthic. Such manipulation can include treatment with agents that are immunosuppressive like glucocorticoids or azathioprine; agents that impede Th2 effects like anti-histamines, anti-cytokines, or recombinant cytokines; and agents that influence intestinal motility like anti-cholinergics or opiates. The animal's diet will be altered to reduce coarse fiber content. The animal may be a rat, pig, hamster, bird or other preparatory animal.

Preparatory animals are raised in specific pathogen-free (SPF) (e.g. specific human pathogen free) environments according to methods known in the art. They are tested to ensure absence of human bacterial, mycobacterial, and viral pathogens. Methods for raising animals in SPF environment and advantage thereof is described in the art, e.g., by M. Michael Swindle (J. Invest. Surg., 9:267-271, 1996, hereby incorporated by reference). Swindle also lists several potential human viral and bacterial pathogens of concern. Accordingly, parasite preparations derived from animals raised in a specific human pathogen free environment would not contain these human pathogens, and as such are patentably distinct from parasite preparations prepared from animals raised in any SPF environment Eggs: Some intestinal helminths are acquired by ingestion of viable eggs. Helminths are maintained in SPF preparatory animals, for example, SPF pigs. To harvest eggs, the animals are given a special diet low in coarse fiber. Animals are given an oral purgative to induce defecation. Stool is collected and enzymatically digested to free eggs. Eggs are isolated from liquefied stool by flotation on density gradients, screen filtration, Visser filtration, or centrifugal elutriation. Preservation of eggs varies with the helminth used. Eggs from helminths that are resistant to dessication are dried, compounded with inert material, incorporated into an enteric capsule, and refrigerated. Eggs from helminths that are susceptible to dessication are preserved by refrigeration in liquid medium or by adding cryoprotectant and freezing in liquid nitrogen. Viable eggs are washed, mixed with chilled lactose-free pudding or other vehicle at the location for delivery. Eggs stored in glycerol-based cryoprotectant may not require washing. Eggs from each lot are tested for hatching rate to determine effective dosing. Eggs from each lot are tested for absence of bacterial and viral pathogens.

Larvae: Some helminths (i.e. hookworms) require a soil maturation phase before they can colonize humans. Eggs from these agents will be incubated under optimal conditions to mature the embryo, or hatch the egg and provide larval forms. Patients can be inoculated by subcutaneous injection or oral ingestion of viable larvae.

Cercariae: Some helminths have complex life cycles that utilize an intermediate host. The intermediate host sheds the form able to colonize humans. Cercariae are the form for trematode helminths (i.e. flukes) shed by intermediate hosts like snails. Cercariae are isolated from colonized snails grown in SPF conditions. Cercariae are washed. These may be preserved by adding cryoprotectant and freezing in liquid nitrogen. Thawed or fresh cercariae are washed and injected subcutaneously to inoculate patients. Samples from each lot are tested for absence of pathogens and to determine effective dose.

Encysted Larvae: Some helminths (e.g. tapeworms) form encysted larvae or cysticerci in intermediate hosts. It is the encysted larval form that initiates human colonization. Encysted larva are removed from intermediate hosts, for example, cattle or fish or plants grown in SPF conditions. Cysts are washed free of remaining host tissue. Cysts may be preserved by adding cryoprotectant and freezing in liquid nitrogen. Cysts are thawed or used fresh, washed, mixed with chilled lactose-free pudding or other vehicle at the location for delivery and fed to individuals. Samples from each lot are tested for absence of pathogens and to determine effective dose.

B. Non-Viable Component Vaccines:

Non-viable components of helminthic parasites provide sufficient Th2 conditioning of the immune response to prevent Th1-mediated pathology. Non-viable components are derived from eggs, larvae or adult worms.

Non-viable, intact schistosome eggs produce a strong Th2 response. Eggs are isolated from livers of preparatory animals (i.e. hamsters) grown under SPF conditions. Eggs are isolated by a method modified from that originally described by Coker and Lichtenberg, 1956, Proceedings of the Soc. For Exp. Biol. & Med. 92:780. The modifications consist of using phosphate buffered saline with glucose instead of 1.7% saline for incubation and washing steps along with decreasing the autolytic digestion time. These changes promote isolation of viable eggs. The method is as follows.

Infect golden hamsters with 1000 to 1500 cercariae. Allow the infection to mature (6 to 7 weeks). Remove the livers from the animals and place in 600 mOsm sterile phosphate buffered saline containing 5% glucose, 100 U/ml penicillin and 100 mg/ml streptomycin. The livers are allowed to autodigest for 24 hours at room temperature. Pulse homogenize the livers at low speed for 3 minutes in a cold Waring blender. Incubate the homogenate with collagenase (2 mg/ml) and trypsin (2 mg/ml) at 32° C. for one hour. Filter the homogenate through 50 and 80-100 mesh sieves to remove clumps of tissue and debris. Recover the eggs from the filtrate by passing over a 325 mesh sieve. The eggs will not pass through the screen. Flush the eggs off of the screen and into a 50 ml polypropylene centrifuge tube. Wash the eggs by repeated low speed (400×g) centrifugation in sterile phosphate buffered saline with 5% glucose. The eggs must be free of any collagenous debris. Count an aliquot of eggs in a 1 ml Sedwick chamber to determine total egg number.

Isolated eggs are suspended in saline and flash frozen in liquid nitrogen without cryoprotectant. This kills the egg. Thawed eggs are injected subcutaneously, intramuscularly or intravenously, or at sites of Th1 inflammation to elicit strong Th2 responses. Eggs from other helminths may also be utilized.

Component vaccines may also be used that employ proteins, lipids, or carbohydrates isolated from parasite eggs. An example is schistosome soluble egg antigens (SEA). The method for preparing schistosome egg antigen has been previously described by Boros and Warren, 1970, J. of Experimental Med. 132:488 and is briefly given below.

Washed eggs are resuspended at 50,000 eggs/ml of phosphate buffered saline. This is transferred to a glass tissue homogenizer. The eggs are homogenized on ice. To insure that all shells are broken and miracidia are disrupted, an aliquot (5 ml) is removed for microscopic inspection. Transfer the homogenate to ultracentrifuge tubes. Centrifuge at 100,000×g for 2 hours at 4° C. Recover the aqueous fraction (SEA) and determine the protein content. Store the SEA in small aliquots at −70.degree. C. This method may require modification to isolate the parasite egg products that most strongly promote Th2 conditioning, i.e., to achieve an optimal effective concentration, (100 µg SEA or 10,000 ova/animal). Eggs or soluble egg components are used to initiate Th2 responses or to boost Th2 responses previously initiated by colonization with viable helminths. Eggs or egg components are tested to confirm the absence of pathogens and endotoxin.

Component vaccines can also be developed from larvae and adult worms of helminthic parasites. Larvae or worms are isolated from preparatory animals grown in SPF conditions. Vaccines that employ non-viable intact organisms or proteins, lipids, or carbohydrates isolated from the helminth are prepared and utilized in a manner similar to that previously described for helminth eggs.

Also encompassed in the present invention are vaccines containing fractions or subfractions of the helminthic parasites, as well as vaccines containing isolated proteins, polynucleotides, carbohydrates, lipids, etc. derived from helminthic parasites according to known methods in the art, e.g., as described in Williams et al., 1994, Leukocytes of patients with *Schistosoma mansoni* respond with a Th2 pattern of a cytokine production to mitogen or egg antigens but with a Th0 pattern to worm antigens. J. Infect. Dis. 170:946; Xu-Amano et al., 1993, Helper T cell subsets for immunoglobulin A responses: oral immunization with tetanus toxoid and cholera toxin as adjuvant selectively induces Th2 cells in mucosa associated tissues. J. Exp. Med. 178:1309; Ausiello et al., 2000, Cell mediated immunity and antibody responses to *Bordetella pertussis* antigens in children with a history of pertussis infection and in recipients of an acellular pertussis vaccine. J. infect. Dis., 181:1989.

For example, fractions or subfractions may be prepared according to w method described in Thaumaturgo et al. (2001, Preliminary Analysis of Sm14 in Distinct Fractions of *Schistosoma mansoni* Adult Worm Extract, Mem. Inst. Oswaldo Cruz vol. 96 suppl. Vol. 96, Suppl.: 79-83, hereby incorporated by reference in its entirety). In this method, *S. mansoni* parasites were obtained by retrograde perfusion with heparinized saline (0.85% NaCl solution), 45 days post-infection (Pellegrino & Siqueira 1956, Tcnica de perfuso para colheita de *Schistosoma mansoni* em cobaias experimentalmente infectadas. Rev Bras Mal D Trop 8: 589-597), and used for preparing the different extracts.

Preparation of adult-worm-derived extract (SE)—Parasites were rinsed in PBS. Living worms were then allowed to stand at room temperature (28° C. to 30° C.) in fresh PBS (phosphate buffered saline) for 2-3 h, and frozen at −20° C. After thawing, PBS suspensions of the worms (1 g worms/10 ml PBS) were filtered through a wire mesh, and centrifuged at 10,000 g for 1 h at 4° C. (Tendler & Scapin 1981, *Schistosoma mansoni* antigenic extracts obtained by different extraction procedures. Mem Inst Oswaldo Cruz 76: 103-109; Tendler et al. 1982, Immunogene and protective activity of an extract of *Schistosoma mansoni*. Mem Inst Oswaldo Cruz 77: 275-283). The protein content of SE was assessed by Lowry's method (Lowry et al. 1951), and stock batches containing 1 mg/ml were stored at −20° C. Male and female extracts were prepared according to the same methodology, with parasites separated immediately after perfusion.

Preparation of a rapidly released "fraction" of adult-worm-derived extract (SEi)—SEi preparation corresponded to the initial step of SE: after perfusion as described for SE, live worms were incubated for 2-3 h at room temperature (28° C. to 30° C.), in PBS. Thereafter, adult worms were filtered from incubation solution (SEi) in a wire mesh.

Preparation of SE2—Adult worms remained from SE initial preparation, were re-stored frozen (−20° C.) in PBS for one week (1 g worms/10 ml PBS). After thawing, PBS suspensions were filtered through a wire mesh, and centrifuged at 10,000 g for 1 h at 4° C.

Parasite antigens can also be extracted as described in FIG. 1 of Thaumaturgo et al. (supra) (reproduced as FIG. 23). Alternatively, parasite antigens may be prepared as described in Deelder et al. (1980. Applicability of different antigen preparations in the enzyme-linked immunosorbent assay for *schistosomiasis mansoni*. Am. J. Trop. Med. Hyg. 29:401-410). For example, antigens may be prepared from soluble worm antigen preparation (SWAP) prepared as soluble supernatant fluids from buffered saline homogenates of the respective life-cycle stage (Goes et al. 1989, Production and characterization of human monoclonal antibodies against *Schistosoma mansoni*. Parasite Immuno) 11: 695-711). SWAP was fractionated by anion-exchange chromatography on FPLC (fast protein liquid chromatography), as previously described (Hirsch & Goes 1996, Characterization of fractionated *Schistosoma mansoni* soluble adult worm antigens that elicit human cell proliferation and granuloma formation in vitro. Parasitology 112: 529-535). Briefly, proteins were eluted with 20 mM Tris-HCl, pH 9.6, in a multistep increasing gradient up to 1 M NaCl, interrupted by hold-gradient intervals at 0, 100, 280, 450, 600 and 750 mM. Flow-through fractions were concentrated by lyophilization. The concentrated material was dialyzed against 0.15 M phosphate-buffered saline (PBS), pH 7.4, sterilized by filtration and stored at −70.degree. C. The protein content was measured according to Bradford microassay (Bradford 1976, A rapid and sensitive method for the quantification of microgram quantities of protein utilizing the principle of protein-dye binding. Analyt Biochem 72: 248-254, hereby incorporated by reference in its entirety). Analysis of the six fractions, separated by 10% SDS-PAGE (sodium dodecyl-sulfate polyacrylamide gel electrophoresis) under reducing conditions (Laemmli 1970, Cleavage of structural proteins during the assembly of the head of bacteriophage T4. Nature 227: 680-685, hereby incorporated by reference in its entirety), showed multiple protein bands, fraction III containing high (97 and 160 KDa), intermediate (52 and 56 KDa) and low (28 and 36 KDa) proteins. This fraction was called PIII and was used in different immunological assays.

Lipids may also be prepared as described in the art, for example, in van der Kleij et al. (1999, Recognition of Schistosome Glycolipids by Immunoglobulin E: Possible Role in Immunity Infection and Immunity, 67: 5946-5950, hereby incorporated by reference in its entirety).

In one embodiment, lipids of *S. mansoni* adult worms (12 g [wet weight]) and eggs (1.6 g [wet weight]) were extracted by the method described by Bligh and Dyer (1959. A rapid method of total lipid extraction and purification. Can. J. Biochem. Physiol. 37:911-917). The organic phase was dried by rotary evaporation, dissolved in 10 ml of chloroform, and applied to a 20-ml column of the anion exchanger TEAE-cellulose (Serva, Heidelberg, Germany) that was converted to the hydroxyl form. Lipids were eluted as described by Rouser et al. (1969. Diethylaminoethyl and triethylaminoethyl cellulose column chromatographic procedures for phospholipids, glycolipids, and pigments. Methods Enzymol. 14:272-317). According to this protocol, the fractions contain the following lipids: fraction 1, cholesterol, glycerides, and other neutral lipids; fraction 2, cerebrosides, glycerol diglycerides, phosphatidylcholine, and sphingomyelin; fraction 3, ceramidepolyhexosides; fraction 4, inorganic substances; fraction 5, phosphatidylethanolamine and free fatty acids; fraction 6, phosphatidylserine; fraction 7, none (washing step); and fraction 8, phosphatidic acid, cardiolipin, phosphatidylglycerol, phosphatidylinositol, and other acidic lipids. The presence of glycolipids in fractions 2 and 3 was confirmed by orcinol staining of the lipid fractions on HPTLC plates (1956. Quantitative estimation of cerebrosides in nervous tissue. J. Neurochem. 1:42-53).

C. Maintenance of Helminth Organisms:

Helminths are cycled through intermediate and preparatory animals grown in SPF conditions. Samples of helminth populations are tested to ensure phenotypic stability such as colonization rates, fecundity, and susceptibility to anti-helminthics.

Dosage, Administration and Pharmaceutical Formulations

Individuals in need of treatment receive the infected form of the parasite (egg, cercariae or larvae) orally or parenterally depending upon the natural life cycle of the parasite selected. Alternatively, soluble worm or egg extracts can be given orally or parenterally to induce TH2 responses.

With regard to intestinal and liver helminths and schistosomes, they begin producing ova that appear in the stool about 30-60 days after inoculation. Quantifying the eggs in the stool proves satisfactory for assessing adequacy and intensity of infection. Aliquots of stool are processed by sucrose floatation to determine the total number of eggs in each specimen. Flotation over sucrose solution is a method frequently used to isolate eggs from stool for accurate counting as reported by Koontz and Weinstock, 1996, Gastroenterology Clinics of N. America, 25:435.

The helminthic parasite compounds of the invention may be formulated for administration in any convenient way, and the invention therefore includes within its scope pharmaceutical compositions comprising the helminthic parasite compound in accordance with the invention adapted for use in humans. Such compositions may be presented for use in conventional manner with the aid of any necessary pharmaceutical carriers or excipients.

The helminthic parasite compound according to the invention may be formulated for injection, and therefore, vaccine use, and may be presented in unit dose form in ampules, or multidose containers, if necessary, with an added preservative. The compositions may also take such forms as suspensions, solutions or emulsions of oily or aqueous vehicles and may contain formulatory agents such as suspending, stabilizing, and/or dispersing agents. Alternatively, the helminthic parasite may be in powder form or reconstituted with a suitable vehicle, e.g. sterile-pyrogen-free water, before use.

If desired, such powder formulation may contain an appropriate non-toxic base in order to ensure that the powder is reconstituted with water, the pH of the resulting aqueous formulation being physiologically acceptable.

The helminthic parasite compounds may also be formulated as suppositories, e.g. containing conventional suppository bases such as cocoa butter or other glycerides.

The helminthic parasite compounds may also be formulated to oral dosage with conventional fillers, carriers, and excipients. The amount of parasite administered to the individual in need thereof is an amount sufficient to prevent or treat the autoimmune disease. This amount may vary depending upon the disease being treated or prevented and the helminthic parasite, whether it is being administered intact, or as an egg, larvae, extract or cercariae.

Typically, when the parasites are administered to prevent or treat or ameliorate the symptoms of a disease, the amount of parasite ranges from about 50 to about 50,000, more particularly from about 500 to about 5,000. The amount of parasite can also range from 100 to about 25,000, 100 to about 20,000, 100 to about 10,000, 500 to about 600, 500 to about 700, 500 to about 800, 500 to about 900, 500 to about 1000, 5000 to about 2000, 500 to about 3000, 500 to about 4000, 500 to about 5000, 500 to about 6000, 500 to about 7000, 500 to about 8000, 500 to about 9000, 500 to about 1000, 500 to about 5000, 1000 to about 2000, 1000 to about 3000, 1000 to about 4000, 1000 to about 5000, 1000 to about 10,000, 1000 to about 20,000 and 1000 to about 50,000. The amount of parasite can also be on the order of 50, 100, 200, 300, 400, 500, 600, 700, 800, 900, 1000, 5000, 10,000, 15,000, 20,000, 25,000, 30,000, 35,000, 40,000, 45,000, 50,000 or more. This amount may range from about 500 to about 10,000, (e.g., 500, 600, 700, 800, 900, 1000, 2000, 3000, 4000, 5000, 6000, 7000, 8000, 9000 and 10,000 or more). In one embodiment, the amount is 2500 to about 5000.

When eggs are utilized, about 500 to about 5000, e.g., 500, 600, 700, 800, 900, 1000, 2000, 3000, 4000, 5000, 6000, 7000, 8000, 9000 and 10,000 or more). The amount may range from about 500 to about 1000, 600 to about 5000, 600 to about 2500, 700 to about 5000, 700 to about 2500 may be utilized to treat GVHD. In one embodiment, the amount is 2500 to about 5000.

When extracts are administered, about 100 µg to about 10,000 µg (e.g., 100 µg, 200 µg, 300 µg, 400 µg, 500 µg, 600 µg, 700 µg, 800 µg, 900 µg, 1000 µg, 2000 µg, 3000 µg, 4000 µg, 5000 µg, 6000 µg, 7000 µg, 8000 µg, 9000 µg, 10,000 µg or more) are utilized to treat the autoimmune diseases. A range of 100 µg to about 5000 µg, 200 µg to about 4000 µg, 300 to about 3000 µg, 400 µg to about 2500, 500 µg to about 2500 may be used.

When larvae and cercariae are administered, the dosages may range from about 500 to about 5,000 in each case, for example, 500 to about 4000, 600 to about 3000, 700 to about 2000, 600 to about 1000, For prevention or vaccine use, the total dose of the amount of the parasites may be 500-5,000, for example 500 to about, 4500, 500 to about 4000, 500 to about 3500, 500 to about 3000, 500 to about 2500, 500 to about 2000, 500 to about 1500, 500 to about 1000, 500-2500, 500-2000, 500-1000.

Dosage of a parasite preparation may be monitored by measuring Th1, Th2 or regulatory cell responses. Alternatively, the dosage may be monitored by evaluating the pathology or symptoms of a particular disease as known in the art or described herein.

A. Determination of Th1 and Th2 Responses

In order to show the efficacy of the present invention, the Th1 and Th2 response may be distinguished. Metawali et al., 1996, J. of Immunol. 157:4546 has shown that in mice, it is possible to distinguish a Th1 from a Th2 response by histologic analysis, and by analysis of cytokine and immunoglobulin profiles. Further, Sandor et al., 1990, J. of Exp. Med. 171:2171 has shown that cell surface expression of Fcg3 and MHC Class II molecules afford discrimination. In this procedure, small bowel and colon are examined histologically to determine the degree of mucosal inflammation, eosinophilia and mastocytosis. The latter cell types are indicative of a Th2 response. Mesenteric lymph nodes (MLN) and spleens can be dissociated into single cell suspensions for in vitro culture in microwell plates. Cells ($1$-$2 \times 10^6$/well) in complete RPMI medium are cultured for up to 72 h in the presence or absence of worm antigen or anti-CD3 and then the supernatants are assayed for cytokines and immunoglobulins. IFN$\gamma$, TNF$\alpha$. and IgG2a characterize a Th1 response, whereas IL-4, IL-5, IgE and IgG1 typify a Th2 reaction. Also, serum can be assayed for cytokine and immunoglobulin concentrations. Furthermore, dispersed inflammatory leukocytes are examined by flow cytometry for Fc$\gamma$3 expression on macrophages (Th1) and MHC Class II expression on B cells (Th2). Controls include serum, MLN and spleens from appropriate age-matched, littermate mice that hosted no parasite.

A similar analysis can differentiate a human Th1 from a Th2 response. One examines inflamed tissue, isolated leukocytes from regions of inflammation and peripheral blood cells. Leukocytes are cultured in vitro alone or in the presence of parasite antigen or mitogens to stimulate cytokine release. IgG2 substitutes for IgG2a.

B. Determination of Regulatory T Cell Activity

Methods of isolating regulatory T cells from in vitro culture or animals are known in the art, for example, as described in McGuirk P, Mills K H. Pathogen-specific regulatory T cells provoke a shift in the Th1/Th2 paradigm in immunity to infectious diseases. Trends Immunol 2002; 23(9):450-5; Field, A. C., L. Caccavelli, M. F. Bloch, and B. Belton. 2003. Regulatory CD8+ T cells control neonatal tolerance to a Th2-mediated autoimmunity. Journal of Immunology. 170:2508-2515; von Herrath M G, Harrison L C. Antigen-induced regulatory T cells in autoimmunity. Nat Rev Immunol. March 2003; 3(3):223-32; Francois Bach J. Regulatory T cells under scrutiny. Nat Rev Immunol. March 2003; 3(3): 189-98; Curotto de Lafaille M A, Lafaille J J. CD4(+) regulatory T cells in autoimmunity and allergy. Curr Opin Immunol. December 2002; 14(6):771-8; McGuirk P, Mills K H. Pathogen-specific regulatory T cells provoke a shift in the Th1/Th2 paradigm in immunity to infectious diseases. Trends Immunol. September 2002; 23(9):450-5; Tung K S, Agersborg S S, Alard P, Garza K M, Lou Y H. Regulatory T-cell, endogenous antigen and neonatal environment in the prevention and induction of autoimmune disease. Immunol Rev. August 2001; 182:135-48; Read S, Powrie F. CD4(+) regulatory T cells. Curr Opin Immunol. December 2001; 13(6):644-9; Yssel H, Lecart S, Pene J. Regulatory T cells and allergic asthma. Microbes Infect. September 2001; 3(11):899-904; Shevach, E. M. 2002. CD4+ CD25+ suppressor T cells: more questions than answers. Nature Reviews Immunology. 2:389-400; Annacker, O. and F. Powrie. 2002. Homeostasis of intestinal immune regulation. Microbes & Infection. 4:567-574; Read, S., V. Malmstrom, and F. Powrie. 2000. Cytotoxic T lymphocyte-associated antigen 4 plays an essential role in the function of CD25(+)CD4(+) regulatory cells that control intestinal inflammation. J. Exp. Med. 192:295-302.

Regulatory T cell response or activity may be measured by an internal marker, a cell surface marker, or a secreted marker as described herein.

Useful internal markers for regulatory T cells include, but are not limited to, transcription factors such as Scurfin, Smad7, Gata3, Tbet (Tbx21).

Useful surface markers for regulatory T cells include, but are not limited to, CD4, $CD45RB^{lo}$, CD45Rc, Cytolytic T lymphocyte associated antigen 4 (CTLA-4), CD25, CD103, Ox40, 4-1BB, CD62L, $\alpha\epsilon\beta$ integrin, latency-associated peptide (LAP) or glucocorticoid induced TNF receptor family related protein (GITR), chemokine receptor CCR5, TI-ST2.

Useful secreted markers for regulatory T cells include, but are not limited to, IL-5, IL-10 and TGFβ.

General Methods

Mice and H. bakeri (polygyrus) administration. Wild type (WT) C57BL/6 (H2b) and Balb/C (H2d) mice (The Jackson Laboratory, Bar Harbor, Me.) as well as a C57BL/6 mouse strain with a T cell-specific defect in TGFβ signaling (TGFβRII DN) (H2b) were utilized (Gorelik, L., and Flavell, R. A. 2000. Immunity.:171-18). Five to 6 week old Balb/C mice were inoculated with 150 H. bakeri (polygyrus) third stage larvae (L3) by oral gavage. Infective H. bakeri (polygyrus) L3 (original specimens archived at the U.S. National Helminthological Collection no. 81930) were obtained from mouse fecal cultures of eggs by the modified Baermann method and stored at 4° C. until used. Mice were housed and handled appropriately following national guidelines and as approved by our Animal Review Committee.

Cell Purification for GVHD Induction.

Donor bone marrow (BM) cells were obtained from the femurs and tibias of uninfected, 5-8 week old C57BL/6 mice and T cells were depleted using mouse panT cell beads (Dynal Biotech) according to the manufacturer's instructions. Donor T lymphocytes (CD3+) were magnetically enriched from splenic single cell suspensions of uninfected, 5-8 week old C57BL/6 and TGFβRII DN mice using the T cell untouched isolation kit (Miltenyi Biotech).

Cell Purification for In Vitro Cultures.

To determine TGFβ cytokine generation of Treg-enriched vs Treg-depleted cultures, CD4+ T cells were purified from splenic and mesenteric lymph node (MLN) single cell suspensions of H. bakeri (polygyrus)-infected and uninfected control Balb/C mice using CD4 T cell untouched isolation kit (Miltenyi Biotech) and separated into CD25 positive and CD25 negative fractions using anti-CD25 PE labeling, followed by magnetic separation with anti-PE beads (Miltenyi Biotech). Enrichment or depletion efficiency was >98% with these techniques (data not shown). To determine helminthic regulation of IFNγ and TNFα cytokine output during GVHD, donor CD3+ T cells were sorted from total anti-CD3 FITC and anti-H2b PE stained splenocytes of uninfected control and H. bakeri (polygyrus)-infected Balb/C recipients 6 days after GVHD induction using FACS Vantage SE DiVa cell sorter (Becton Dickinson).

GVHD Induction.

Three week helminth-infected and uninfected control Balb/C recipients (H2d) underwent total body irradiation from a Cs137 source (850 cGy in 2 separate doses given 4 hours apart) and were administered $10 \times 10^6$ TCD-BM cells and $1.5 \times 10^6$ splenic T lymphocytes from uninfected control C57BL/6 WT donors. To characterize the role of TGFβ signaling in helminth-induced regulation of donor T cell-mediated GVHD, $1.5 \times 10^6$ donor splenic T cells from TGFβRII DN mice were administered along with $10 \times 10^6$ TCD BM cells from C57BL/6 WT mice into uninfected control and 3 week H. bakeri (polygyrus)-infected Balb/C recipients. Mice were monitored daily for survival for >70 days. The disease severity was scored daily based on animal weight, posture, activity, fur texture and skin integrity (38-40). In parallel experiments, uninfected control and helminth-infected mice were sacrificed 6 days after GVHD induction for cellular and histological analysis.

Flow Cytometry.

Six days after GVHD induction, uninfected control and H. bakeri (polygyrus)-infected mice were sacrificed. Spleen and MLN were isolated for cellular analysis. For surface staining, cells were suspended at $2 \times 10^7$ cells/ml in PBS with 2% FCS and Fc receptors were blocked with 2.4G2 mAb. Cells were stained with various combinations of anti-CD3 FITC, anti-CD3 PE-Cy7, anti-CD4 PE-Cy7, anti-LAP PE (eBioscience), anti-H2b PE, anti-H2d PE, and anti-H2b APC (BD Biosciences). For the intracellular FoxP3 staining, cells were stained with anti-FoxP3 FITC, anti-FoxP3 PE or FoxP3 APC using FoxP3 staining buffer (eBioscience) according the manufacturer's instructions.

In Vitro Cell Culture and Cytokine ELISA.

To determine TGFβ secretion of FoxP3+ Treg-enriched and Treg-depleted CD4 T lymphocytes, magnetically purified CD4+CD25+ or CD4+CD25− splenic and MLN cells from uninfected control as well as H. bakeri (polygyrus)-infected Balb/C mice without GVHD were stimulated with plate-bound anti-CD3 and soluble anti-CD28 (each 1 μg/ml) (eBioscience) for 48 hours in cell culture medium with 1% FCS and 1 mg/ml BSA (Ince, M. N., Elliott, D. E., Setiawan, T., Metwali, A., Blum, A., Chen, H. L., Urban, J. F., Flavell, R. A., and Weinstock, J. V. 2009. *Eur. J. Immunol.*:1870-1878; Ince, M. N., Elliott, D. E., Setiawan, T., Blum, A., Metwali, A., Wang, Y., Urban, J. F., Jr., and Weinstock, J. V. 2006. *J. Immunol.*:726-729.) TGFβ cytokine concentration in acidified and re-alkalinized supernatants was determined using antibody pairs from R&D Systems according to manufacturer's instructions. Results were displayed after subtracting the TGFβ concentration of culture supernatants from TGFβ concentrations of the culture media. To determine helminthic regulation of donor T cell IFNγ and TNFα secretion, sorted donor splenic T cells (CD3+ and H2b+) from uninfected control and *H. bakeri* (polygyrus)-infected Balb/C mice with GVHD were stimulated with plate-bound anti-CD3 and soluble anti-CD28 (each 1 µg/ml) for 48 hours in lymphocyte growth medium containing 10% FCS (Setiawan, T., Metwali, A., Blum, A. M., Ince, M. N., Urban, J. F., Jr., Elliott, D. E., and Weinstock, J. V. 2007 *Infect. Immun.* 4655-4663.). Supernatants were analyzed for IFNγ and TNFα content using antibody pairs from R&D Systems. Similarly, sera isolated from uninfected control and *H. bakeri* (polygyrus)-infected Balb/C mice 6 days after GVHD induction were analyzed for IFNγ and TNFα cytokines.

Histopathology.

Six days after GVHD induction, colons, lungs and livers from uninfected control or *H. bakeri* (polygyrus)-infected mice were fixed in 4% neutral buffered formalin, processed and 6 µm sections were stained with hematoxylin and eosin. Tissues were analyzed for GVHD-related inflammation and the severity of inflammation was scored in blinded fashion by MNI, ANH and DEE (38; 41-44). GVHD-related colitis was graded based on the degree of inflammation and the frequency of crypt apoptosis. Inflammation is graded as none (score: 0), mild (1), moderate (2), severe without ulcer (3) and severe with ulcer (4). Crypt apoptosis was graded as rare (score: 0), occasional per 10 crypts (1), few per 10 crypts (2), majority of crypts containing apoptotic bodies (3), majority of crypts containing more than 1 apoptotic bodies (4). The minimal score in this grading system for colonic disease was 0 and the maximum score 8. GVHD-related lung inflammation was graded based on the presence of perivascular cuffing, vasculitis, peribronciolar cuffing and alveolar hemorrhage. The minimal score in this grading system for lung inflammation was 0 and maximum 4.

Statistical Analysis.

Differences in survival between groups were determined by Kaplan Meier's log rank test. Differences in cell number and composition, serum IFNγ, TNFα content, differences in splenic donor T cell IFNγ, TNFα generation, differences in TGFβ cytokine output of in vitro stimulated cell cultures and histopathological GVHD scores between groups were determined using Student's t test.

Animals.

Colonies of 129/SV IL-10−/− mutant mice, and appropriate control animals are maintained are housed in facilities maintained as a specific pathogen-free environment according to standard methods.

Parasite Maintenance, Animal Infection, Production of Schistosome Eggs.

The maintenance of *T. muris* and the method used for infection are as described by Else and Wakelin, 1990, Parasitology, vol. 100, part 3: 479.

Schistosome eggs were harvested from the livers of schistosome-infected hamsters and stored as described by Elliott, 1996, Methods: A Companion to Methods in Enzymology, 9:255. Five infected hamsters yield about $2 \times 10^6$ eggs.

Preparation of *T. suis* Eggs

The following process was used in the preparation and harvesting of *T. suis* eggs. Adult *T. suis* worms were isolated from the colon of pigs 7-8 wks after exposure to an experimental inoculation of *T. suis* eggs. Embryonated eggs were obtained by culturing adult worms in vitro, and then the excreted eggs, separated from the culture medium by centrifugation, were placed into 0.2% potassium dichromate solution at 22° C. for 5-6 wks with bubbling to obtain infective first-stage larvae. Eggs were washed twice in sterile water by centrifugation at 1200×g for 10 min, counted, and re-suspended in the desired amount of saline based on a calculated dose of 2,500. These eggs were stored for use in the subjects. The ova are stable for at least one year in the refrigerator. To assure infectivity, we monitored patients for the appearance of ova in the stool after colonization. The number of ova in the stool is proportional to the intensity of the infestation. Also, from time to time, we infect pigs with our stored ova to assure continued infectivity.

Infection with *M. avium*.

Mice were infected by injecting $10^6$ colony forming units (CFU) of *Mycobacterium avium* (ATCC 25291) intraperitoneally. On day 60 of infection, some mice also received 35 *S. mansoni* cercariae to induce dual infection.

Schistosome Infection and Isolation of Ova.

Some experiments used mice (18-20 g) infected for 8-9 wks with *S. mansoni*. Mice were infected subcutaneously with 40 cercariae from the Puerto Rican strain.

Granuloma Isolation and Dispersal.

Granulomas form in schistosome-infected mice because of natural egg deposition, which begins at the 6th wk of infection. *M. avium* also induces granulomas. We study liver granulomas isolated from infected mice as described (Elliott, 1996, supra). Granulomas were dispersed to produce single-cell suspensions. Isolated granulomas were agitated for 35 min at 37° C. in a shaker water bath in RPMI medium containing 5 mg/ml collagenase. The residual granulomas were sucked and expelled through a 1 ml syringe to induce further dissociation. The resulting cell suspension was filtered through gauze and washed three times. Cell viability was determined by Eosin-Y exclusion. This protocol resulted in a high yield of viable inflammatory cells that show preserved surface molecule expression.

Spleen and MLN Dispersal

Splenocytes and MLN were dispersed by teasing and washing the tissue through a stainless steel mesh. The contaminating RBC were lysed with H20, and the cells were washed ×3 in RPMI before use.

Evaluation of Mucosal Inflammation

To grade intestinal inflammation, tissue was removed at the indicated time points, Swiss-rolled and embedded in paraffin according to standard methods. The sections were stained with hematoxylin and eosin. The degree of colonic inflammation was graded semiquantitatively from 0 to 4 in a blinded fashion by a single pathologist using our usual standardize technique (1 9). 0=no inflammation, 1=low level inflammation, 2=intermediate level, 3=high level inflammation with wall thickening, 4=transmural infiltration, loss of goblet cells, wall thickening.

Cell Isolation and T Cell Enrichment

Th1, Th2, and regulatory T cells may be isolated according to methods known in the art, e.g., as described in Current Protocols in Immunology (2001, Eds. John E. Coligan, Ada M. Kruisbeek, David H. Margulies, Ethan M. Shevach, Warren Strober, published by John Wiley & Sons)

In one embodiment, single cell suspensions of MLN were prepared by gentle teasing in RPMI 1640 medium (GIBCO, Grand Island, N.Y.). The cells were briefly re-suspended in distilled water to lyse RBC. The MLN then were washed three times in a large volume of RPMI.

Gut LPMC were isolated as described below. Intestinal tissue was washed extensively with RPMI, and all visible Peyer's patches were removed with a scissors. The intestine was opened longitudinally, cut into 5 mm pieces and then incubated in 0.5 mM EDTA in calcium and magnesium free Hanks' for 20 min at 37° C. with shaking to release intraepithelial lymphocytes and epithelial cells. This was repeated after thorough washing. Tissue then was incubated 20 min at 37° C. in 20 ml RPMI containing 10% FCS, 25 mM HEPES buffer, 2 mM L-glutamine, $5 \times 10^5$ M B-mercaptoethanol, 1 mM sodium pyruvate, 100 U/ml penicillin, 5 mg/ml gentamycin, and 100 mg/ml streptomycin (all GIBCO) and 1 mg/ml collagenase (Sigma #CO130). At the end of the incubation, the tissue was subjected to further mechanical disruption using a 1 ml syringe. To remove debris, the LPMC preparations were washed through a pre-wet gauze layered in a funnel with RPMI. Then, the LPMC were washed once and were sieved through a pre-wet 2 cm nylon wool column gently packed into a 10 ml syringe. After washing, cells (up to $2 \times 10^7$) were layered onto a column of Percoll with a 30:70% gradient. Cells were spun at $2200.\text{times.G}$ at room temperature for 20 min. The LPMC collected from the 30:70 interface were washed and maintained on ice until used. Cell viability was 90% as determined by eosin Y exclusion.

For cell transfer experiments, MLN T cells were isolated by negative selection using the SpinSep enrichment procedure employing antibody-coated, dense particles as described by the manufacturer (#17031, #17032, Stem Cell Technologies, Vancouver, Canada). Flow cytometry was used after each separation to assure appropriate recovery and purity (>98%) of the Thy+ T cells.

Cell Transfer.

MLN cells were isolated from IL10-/- mice colonized 2 wks with *H. polygyrus* or from age-matched healthy IL10-/- mice without such colonization. These unfractionated, dispersed MLN cells ($2 \times 10^7$ cells/mouse) or MLN T cells ($5 \times 10^6$ cells/mouse) then were transferred into colitic IL10-/- mice 2 days after discontinuation of piroxicam treatment by ip injection. The colitis was evaluated 14 days later.

Additional Methods for Regulatory T Cell Preparation

In some embodiments of the present invention, regulatory t cells may be prepared from cultured cells or an animal for further analysis according to methods known in the art, e.g., as described in U.S. patent applications with Ser. Nos. 2003/0170648, 2003/0157057, 2003/0133936, 2003/0064067, 2003/0049696, 2002/0182730, 2002/0090724, 2002/0090357, the entirety is hereby incorporated by references.

In vivo sources of cell populations useful as a source of cells include, but are not limited to peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, and the like. The donor is preferably human, and can be fetal, neonatal, child, adult, and may be normal, diseased, or susceptible to a disease of interest.

For example, the regulatory T cells of the present invention can be enriched on the basis of expression of cell surface markers. In one embodiment, the cells are positively selected for expression of CD4 and CD25, and can be negatively selected for the absence of CD45RA. Optionally, other markers can be used to further separate subpopulations of the Treg cells, including CD69, CCR6, CD30, CTLA-4, CD62L, CD45RB, and CD45RO. The methods can include further enrichment or purification procedures or steps for cell isolation by positive selection for other cell specific markers. In another embodiment, regulatory T cells are separated from a complex mixture of cells by techniques that enrich for cells having the characteristics of being $CD4^+CD25^+$, and optionally $CD45RA^-$. For isolation of cells from tissue, an appropriate solution may be used for dispersion or suspension. Such a solution will generally be a balanced salt solution, e.g. normal saline, PBS, Hanks balanced salt solution, etc., conveniently supplemented with fetal calf serum, BSA, normal goat serum, or other naturally occurring factors, in conjunction with an acceptable buffer at low concentration, generally from 5-25 mM. Convenient buffers include HEPES, phosphate buffers, lactate buffers, etc.

In another embodiment, separation of regulatory T cell population then uses affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, LDS). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

In one embodiment, the antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody, i.e. using a saturating amount of antibody. The appropriate concentration can also be determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The staining intensity of cells can be monitored by flow cytometry, where lasers detect the quantitative levels of fluorochrome (which is proportional to the amount of cell surface antigen bound by the antibodies). Flow cytometry, or FACS, can also be used to separate cell populations based on the intensity of antibody staining, as well as other parameters such as cell size and light scatter. Although the absolute level of staining may differ with a particular fluorochrome and antibody preparation, the data can be normalized to a control.

The labeled cells are then separated as to the expression of CD4 and CD25. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for human Treg activity may be achieved in this manner. The subject population will be at or about 70% or more of the cell composition, and usually at or about 90% or more of the cell composition, and may be as much as about 95% or more of the cell population. The enriched cell population may be used immediately. Cells can also be frozen, although it is preferable to freeze cells prior to the separation procedure, or may be frozen at liquid nitrogen temperatures and stored for long periods of time, being thawed and capable of being reused. The cells will usually be stored in DMSO and/or FCS, in combination with medium, glucose, etc. Once thawed, the cells may be expanded by use of growth factors, antigen, stimulation, dendritic cells, etc. for proliferation and differentiation.

Cell Culture.

For cytokine analysis, cells were cultured for 48 h in 96 well microliter plates (Corning, Cambridge, Mass.) with 200 µl of medium ($5\times10^5$ Cells/well) at 37° C. The culture medium was RPMI containing 10% FCS, 25 mM HEPES buffer, 2 mM L-glutamine, $5\times10^5$ M b-mercaptoethanol, 1 mM sodium pyruvate, 100 U/ml penicillin, 5 mg/ml gentamycin, and 100 mg/ml streptomycin (all GIBCO). For most experiments, the cells were cultured alone or with anti CD3 (2C11, ATCC) and anti-CD28 mAb (Pharminogen, San Diego, Calif.)(each at 1 mg/ml). Isolated T cells were cultured in wells previously coated overnight with anti-CD3 and -CD28 mAb. For IL12 analysis, cells were cultured with the synthetic phosphorothioate backbone oligonucleotide ODN 1826 (TCCATGACGTTCCTGACGTT) (SEQ ID NO:4) that contains two (underlined) immunostimulatory CpG motifs (13; 14), provided by the Coley Pharmaceutical Group (Wellesley, Mass.), and used at 0.6 mg/ml to stimulate production.

Dosage and Modes of Administration

The helminthic parasite compound may be formulated for injection and presented in unit dose form in ampules, or multidose containers and can also take the form of suspensions, solutions or emulsions of oily or aqueous vehicles and may contain formulatory agents such as suspending, stabilizing, and/or dispersing agents. Alternatively, the helminthic parasite may be in powder form or reconstituted with a suitable vehicle, e.g. sterile pyrogen-free water, before use."

Soluble worm or egg extract preparations of the invention are administered orally or parenterally depending upon the natural life cycle of the parasite selected. The parasite preparations of the invention can be administered by injection subcutaneously, The compositions of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

The helminthic preparations of the present invention can be administered by any suitable route including but not limited to by injection, by topical or mucosal application, by inhalation or via the oral route including modified-release modes of administration.

Depending on the specific condition being treated, the helminthic parasite preparations of the invention may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, transcutaneous, intradermal, intramedullary delivery (e.g., injection), as well as intrathecal, direct intraventricular, intravenous, intraperitoneal, intranasal, or intraocular delivery (e.g., injection).

Suitable diluents according to the invention include but are not limited to saline. For injection, the bioactive agents of the invention may be formulated in aqueous solutions, suitably in physiologically compatible buffers such as Hanks' solution, Ringer's solution, or physiological saline buffer.

Viable eggs can be mixed with chilled lactose-free pudding or other vehicle at the location for delivery and fed to the subject. Eggs stored in glycerol-based cryoprotectant may not require washing prior to administration.

The compositions of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

The compositions of the invention can be formulated as a liquid, tablet, capsule, caplet, suspension, drops, in a prefilled intravenous bag, in a preloaded syringe, in a patch form, in a time release form, in a single dose formulation, in a vial, or container designed to allow subject to self-administer orally and orally via a capsule that dissolves in the intestine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Helminth Treatment of the Recipient Reduces Disease Activity and the Inflammatory Infiltrate in Acute GVHD FIG. 1 demonstrates that Helminths regulate acute GVHD in mice. (A) *Heligmosomoides bakeri* (polygyrus) infection protects mice from the severe inflammation during acute GVHD. Six days after BMT, *H. bakeri* (polygyrus)-infected animals (*H. bakeri*) displayed less skin discoloration or hunching body posture compared to uninfected mice (Control) with representative examples displayed. (B) Kaplan Meier survival curves of *H. bakeri* (polygyrus)-infected (open squares) or uninfected (closed squares) Balb/C recipients transferred TCD-BM and total splenic T cells from C57BL/6 mice. Cumulative data from three independent experiments with 9 animals in control and 10 mice in the *H. bakeri* group ($p<0.0001$). (C) The weight change in these mice during the entire follow-up of the survival experiment (p=not significant (NS)). (D) The disease score between the control (N=9) and *H. bakeri*-infected mice (N=10) over the entire course of the survival experiment ($p<0.005$).

Figure 1B:
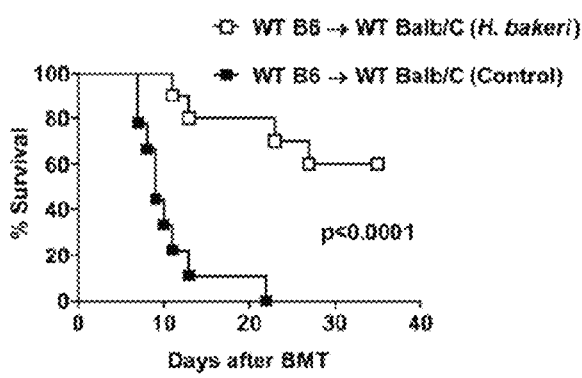
Figure 1C:
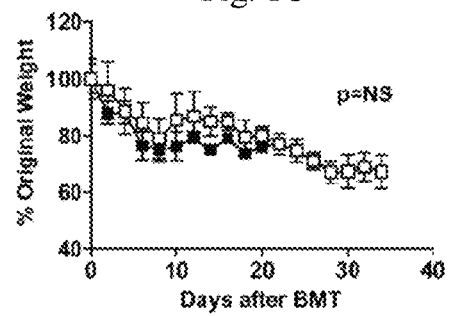
Figure 1D:
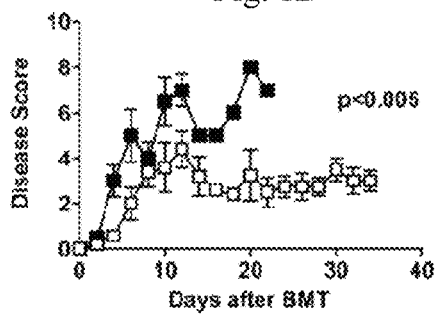

Acute GVHD was initiated in uninfected control or 3 week *H. bakeri* (polygyrus)-infected irradiated Balb/C recipients by transfer of total splenic T cells and T cell depleted (TCD)-BM cells from uninfected donor C57BL/6 mice. Mice started to display signs of GVHD 4-5 days later with this regimen and GVHD was characterized by loss of activity, skin discoloration, hunched body posture, and bloody diarrhea (Cooke, K. R., Kobzik, L., Martin, T. R., Brewer, J., Delmonte, J., Jr., Crawford, J. M., and Ferrara, J. L. 1996. Blood:3230-3239). Uninfected mice displayed more severe GVHD compared to a relatively normal appearance of *H. bakeri* (polygyrus)-infected controls (FIG. 1A). *H. bakeri* (polygyrus) colonization of the recipient was associated with a significant increase in survival ($p<0.001$) (FIG. 1B). Although weight loss associated with GVHD was not different between uninfected and *H. bakeri* administered recipients (FIG. 1C), helminth-infected mice exhibited significantly decreased disease activity ($p<0.005$) (FIG. 1D).

Parallel groups of uninfected control and *H. bakeri* (polygyrus)-administered mice were sacrificed at day six after GVHD induction and tissues were analyzed by histopathology. FIG. 2 demonstrates that Helminth infection is associated with decreased GVHD-related inflammatory changes in the colon and the lungs. Six days after BMT, colons from control (A and B) and helminth-infected (D and E) mice were isolated, fixed and histopathological analysis was performed in 6 μm thick sections under low (10×) (A and D) and high (40×) (B and E) power of magnification. The amount of inflammation and the number of apoptotic bodies in intestinal epithelium (*) was significantly decreased in *H. bakeri* (polygyrus)—infected mice (D and E) compared to uninfected controls (A and B). (G) Severity of colonic inflammation in colons from uninfected and *H. bakeri*-infected mice is graded as described in Materials and Methods. Representative images (A, B, D, E) and statistical analysis (G) of colon tissues from 10 uninfected control and 10 *H. bakeri* (polygyrus)-infected mice from 3 independent experiments; the mean colonic GVHD score±SD ($p<0.0001$). Similarly, lungs from control (C) and helminth-infected (F) mice were isolated where histopathological analysis was performed in 6 μm thick sections under low power magnification (20×). Severity of inflammation in the lungs is graded as described in Materials and Methods. Dense inflammatory infiltrates (*) in control samples (C) was significantly decreased in lungs from helminth-infected mice (F). Representative images (C and F) and statistical analysis (H) of GVHD-related inflammation in the lung from 6 uninfected control and 6 *H. bakeri* (polygyrus)-infected mice from 2 independent experiments; the mean lung GVHD score±SD ($p<0.0001$).

Gut colonization with *H. bakeri* (polygyrus) was associated with reduced inflammatory infiltrates in the colon (mean inflammatory score 2.4±0.8 in *H. bakeri* (polygyrus)-infected mice vs. 5.7±1.4 in uninfected mice; N=10/group for uninfected and helminth-infected; $p<0.001$) (FIG. 2). No inflammation was evident in helminth-infected or uninfected Balb/C mice without GVHD induction (FIG. 10). Numerous apoptotic bodies were evident in colonic samples from control mice and not in samples from *H. bakeri* (polygyrus)-infected mice. Lung tissues from control mice were characterized by dense mononuclear cell infiltrates as well as alveolar hemorrhages, while samples from *H. bakeri* (polygyrus)-administered animals showed fewer infiltrates with preservation of the air sacs (mean inflammatory score 3.5±0.5 in *H. bakeri* (polygyrus)-infected mice vs. 1.5±0.5 in 10 uninfected mice; N=6/group for uninfected and helminth-infected; $p<0.001$) (FIG. 2). Liver tissues from uninfected control or *H. bakeri* (polygyrus)-infected mice showed mild focal portal infiltrates with no difference between groups (data not shown).

Example 2

Helminth Infection is Associated with the Persistence of Recipient T Cells

Figure 12:
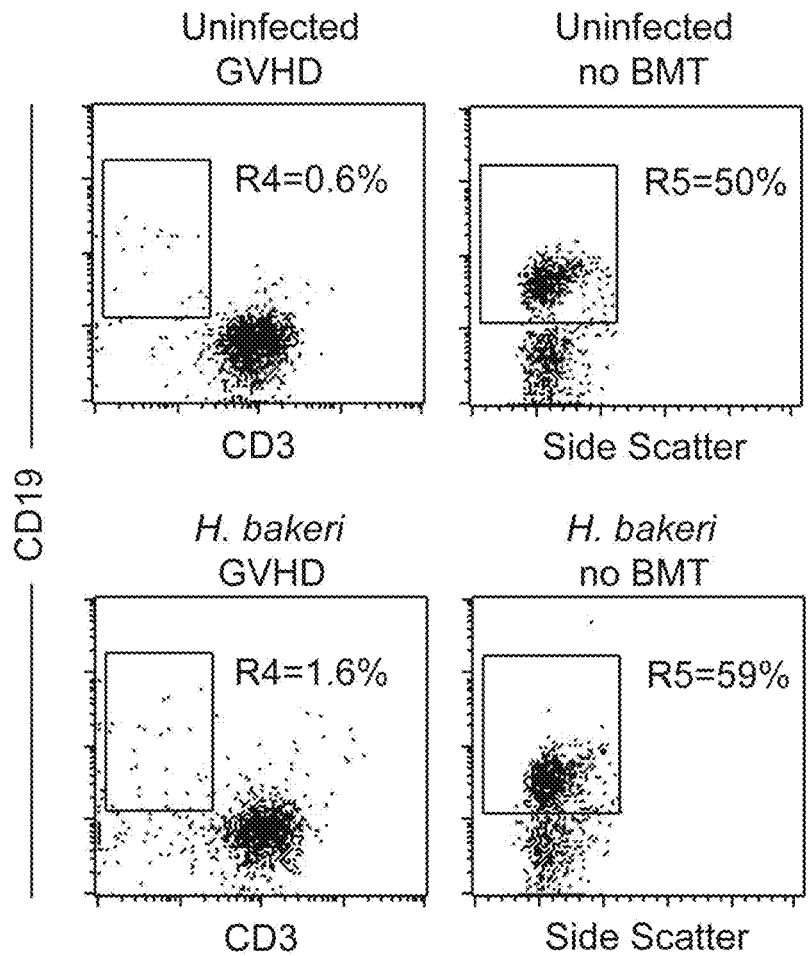
FIG. 12 presents data demonstrating that no B cells were evident in uninfected control or helminth-infected mice during the early expansion phase of donor T cells in GVHD. Spleen cells from uninfected control and *H. bakeri*-infected mice were stained for CD19 and CD3 6 days after GVHD induction (left). The percentage of CD19+ cells are displayed in R4 gate in each dot plot. Representative example from 2 experiments, each experiment utilizing 2 uninfected control and 2 helminth-infected mice. Parallel positive control single color CD19 staining was performed using splenocytes from uninfected control and helminth-infected Balb/C mice with no BMT (right), with the R5 gate showing the percentage of CD19+ cells.

At day six after GVHD induction, the spleen and mesenteric lymph node (MLN) cells were analyzed for donor and recipient markers. FIG. 3 demonstrates that Helminths do not interfere with the expansion of donor T cell graft and promote the survival of recipient T cells. (A) Splenic (upper row) and MLN (lower row) CD3+ T cells isolated 6 days after BMT from *H. bakeri* (polygyrus)-infected mice (right)

display a population of cells that does not stain for the donor marker H2b, while T cells from uninfected control recipients with GVHD (left) uniformly stain for H2b. The percentage of cells in the corresponding quadrants is shown. Representative example from multiple experiments. (B) Splenic (upper row) and MLN CD3+ T cells (lower row) isolated 6 days after BMT from *H. bakeri* (polygyrus)-infected mice (right) display a population of cells positive for the recipient marker H2d, while very few cells from uninfected control recipients with GVHD (left) stain for the recipient marker. The percentage of cells in the corresponding quadrants is shown. Representative example from multiple experiments. (C) Statistical analysis of the percentage of splenic (left) and MLN (right) recipient T cells with N representing the number of mice utilized cumulatively in multiple experiments ($p<0.0001$ for recipient splenic T cells and $p<0.001$ for recipient MLN T cells). Most splenic or MLN cells in uninfected control or *H. bakeri* (polygyrus)-infected mice were CD3 positive T lymphocytes (FIG. 3). No B cells were seen by CD19 staining (FIG. 12). While almost the entire T cell population in spleen or MLN was donor-derived in uninfected control mice, 9±2% of splenic and 16±2% of MLN cells were H2d+ host cells in *H. bakeri* (polygyrus)-infected mice (FIG. 3).

Example 3

Helminths Decrease Donor T Cell Inflammatory Cytokine Generation but do not Interfere with the Engraftment or Early In Vivo Expansion of Donor CD3+ T Cells FIG. 4 demonstrates that Helminth infection is associated with the expansion of regulated donor T cells and regulation of IFNγ and TNFα generation. (A) The number of splenic (left) and MLN (right) donor T cells were calculated using the total number of cells isolated from uninfected control and *H. bakeri* (polygyrus)-infected mice 6 days after BMT and the percentage of H2b+ CD3+ cells, with N representing the number of mice from multiple experiments (p=NS between groups for spleen or MLN donor T cells). (B) Six days after BMT, splenic donor T cells from uninfected control or *H. bakeri* (polygyrus)-colonized mice were FACS-sorted as described in Methods and seeded in triplicate, as 105 cells per well of anti-CD3 coated U-bottom shaped 96-well plates. IFNγ (left) and TNFα (right) from 48 hour anti-CD3/28-stimulated culture supernatants were analyzed by ELISA. Mean cytokine production from 3 independent experiments was calculated from the mean cytokine production in each experiment done in triplicates and data are displayed as mean±SEM. * $p<0.05$ btw uninfected control and *H. bakeri* (polygyrus)-infected groups for IFNγ and TNFα. (C) Serum IFNγ and TNFα levels from uninfected control and *H. bakeri* (polygyrus)-infected animals (N=the number of mice) were analyzed by ELISA. Results are displayed as mean±SEM. *$p<0.05$ btw uninfected control and *H. bakeri* groups for IFNγ and TNFα.

Figure 4A:
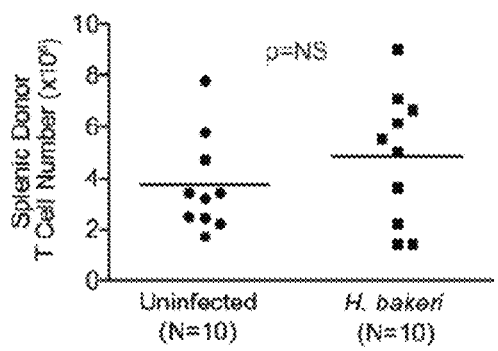
FIGS. 4A-4F demonstrates that Helminth infection is associated with the expansion of regulated donor T cells and regulation of IFNγ and TNFα generation The number of splenic (left) (A) and MLN (right) (B) donor T cells; IFNγ (left) (C) and TNFα (right) (D) production from uninfected control and *H. bakeri* (polygyrus)-infected groups; Serum IFNγ (E) and TNFα (F) levels from uninfected control and *H. bakeri* (polygyrus)-infected animals (N=the number of mice)).
Figure 4B:
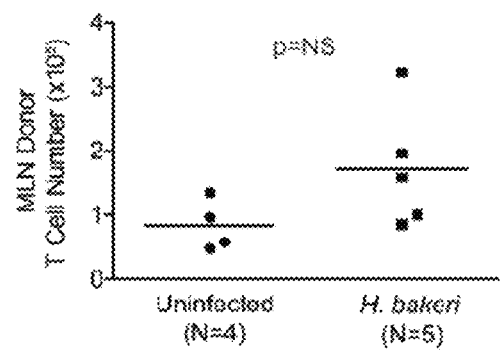
Figure 4C:
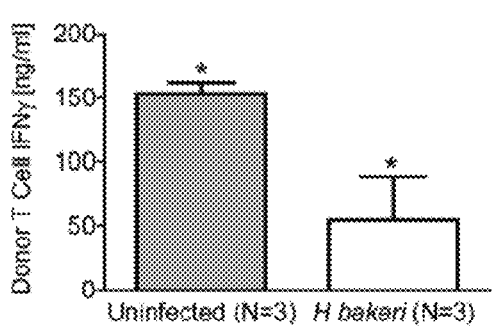
Figure 4D:
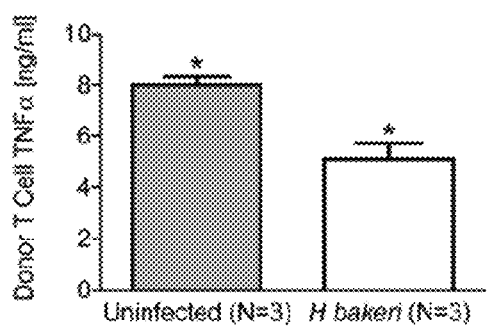
Figure 4E:
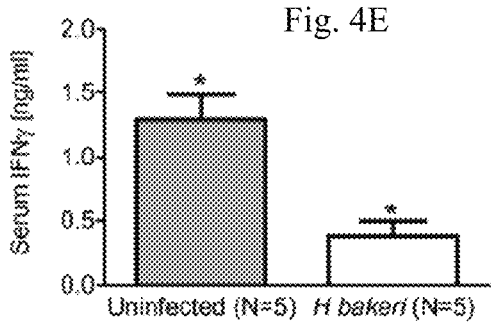
Figure 4F:
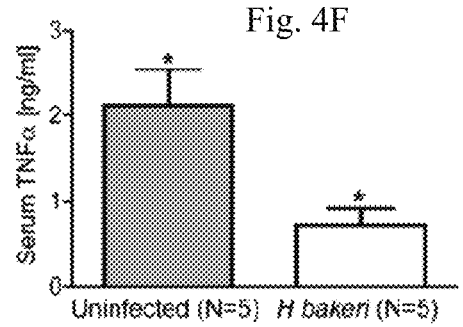

The number of splenic or MLN donor T cells was not different in helminth-infected recipients compared to uninfected controls (FIG. 4A). To determine the effect of helminth infection on donor T cell inflammatory cytokine production, equal numbers of FACS-sorted splenic donor T cells from uninfected control and *H. bakeri* (polygyrus)-infected recipients were isolated 6 days after GVHD induction and studied for in vitro cytokine output. Helminth infection led to reduced anti-CD3/28-stimulated donor T cell IFNγ and TNFα production (FIG. 4B). A parallel decrease in serum IFNγ and TNFα was observed in helminth-infected mice (FIG. 4C). Thus, *H. bakeri* (polygyrus) infection regulated donor T cell inflammatory cytokine production without suppressing the engraftment and early expansion of donor T cells.

Example 4

Helminths Increase the Percentage of Donor and Recipient FoxP3+ Tregs

Figure 5:
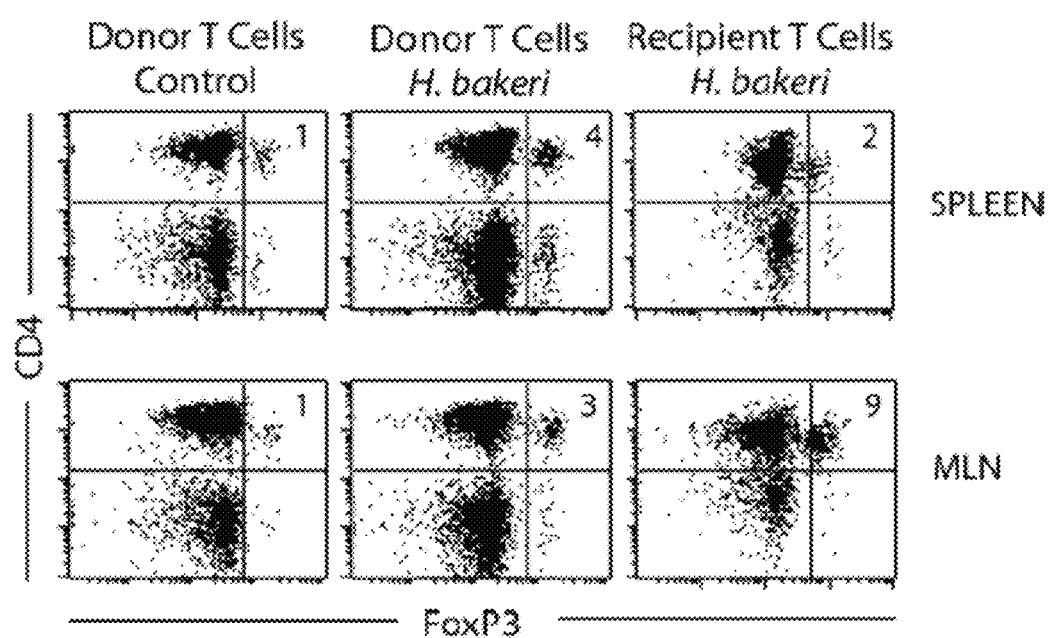
FIG. 5 demonstrates that Helminths increase the percentage of donor and recipient FoxP3+ Tregs. Spleen and MLN cells from uninfected control and helminth-infected mice were stained for CD3, CD4, H2b, H2d and FoxP3. Representative dot plots from spleen (upper row) and MLN (lower row) cells isolated from uninfected control and *H. bakeri* (polygyrus)-infected mice 6 days after BMT. Cells are gated on donor (left and middle columns) or recipient (right column) CD3+ T cells. The percentage of FoxP3+ CD4 T cells are displayed in each dot plot.
Figure 6A:
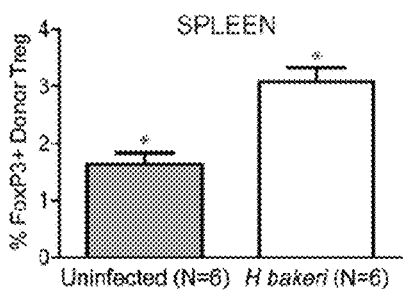
FIGS. 6A-6H demonstrates that Helminths increase the number of splenic and MLN FoxP3+ Tregs. The percentage of donor (A) and recipient (C), splenic FoxP3+ Tregs from uninfected control and *H. bakeri* (polygyrus)-infected mice was analyzed as described in FIG. 5. The percentage of donor (E) and recipient (G) MLN FoxP3+ Tregs from uninfected control and *H. bakeri* (polygyrus)-infected mice was analyzed as described in FIG. 5. The percentage of donor (E) and recipient (G) MLN FoxP3+ Tregs from uninfected control and *H. bakeri* (polygyrus)-infected mice was analyzed as described in FIG. 5. The number of FoxP3+ splenic donor (B) or recipient (D) Tregs per mouse was calculated using the total number of cells isolated from uninfected control and *H. bakeri* (polygyrus)-infected mice 6 days after BMT and the percentage of FoxP3+ CD4+ recipient or donor cells gated on CD3+ lymphocytes (N=Number of mice for the analysis of splenic FoxP3+ Tregs and N=Number of experiments, each utilizing cumulative cells from multiple mice for MLN FoxP3+ Tregs). Data are displayed as mean±SEM (*p<0.05 btw uninfected control and *H. bakeri* (polygyrus)-infected spleen or MLN FoxP3+ donor Treg percentage and total number). As we did not analyze the FoxP3+ recipient Treg percentage and number from uninfected mice due to low numbers of events, no statistical analysis was performed between uninfected control and *H. bakeri* groups for percentage and number of recipient FoxP3+ Tregs. The number of FoxP3+MLN donor (F) or recipient (H) Tregs per mouse was calculated using the total number of mice utilized in each experiment, the total number of cells isolated from pooled MLN cells of uninfected control and *H. bakeri*-infected mice and the percentage of FoxP3+ CD4+ cells gated on CD3+ lymphocytes.
Figure 6B:
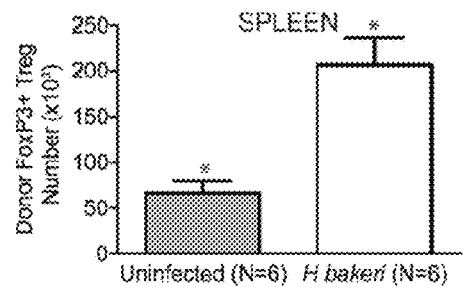
Figure 6C:
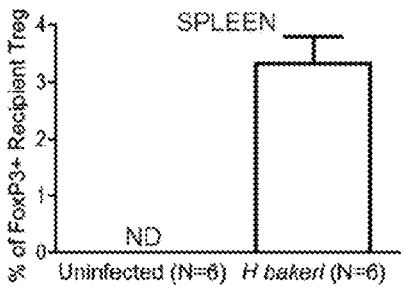
Figure 6D:
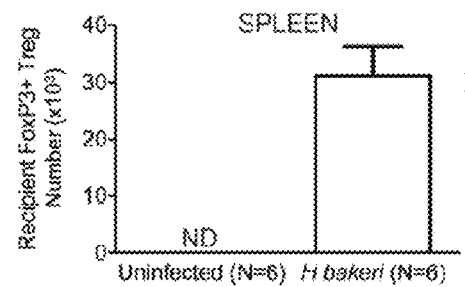
Figure 6E:
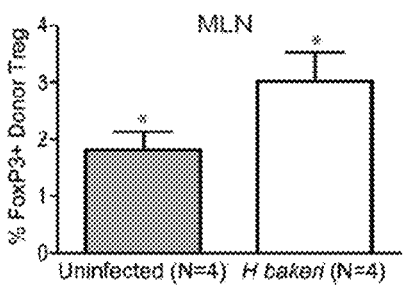
Figure 6F:
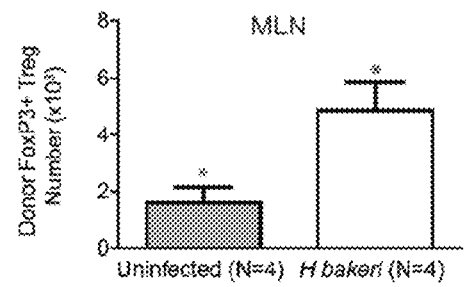
Figure 6G:
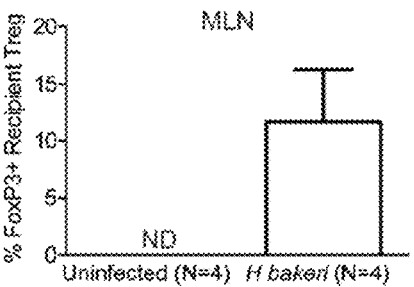
Figure 6H:
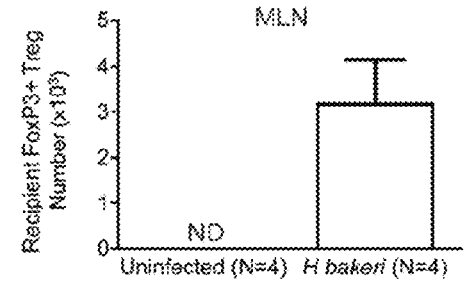

FoxP3+ regulatory T cells have been shown to regulate GVHD (29). To determine whether helminthic regulation of GVHD is associated with the induction of regulatory T cells (Treg), the percentage and total numbers of donor- or recipient-derived Tregs in the spleen and MLN of uninfected control and *H. bakeri* (polygyrus)-infected mice were analyzed. Helminth infection led to a significant increase in the percentage and number of donor as well as recipient FoxP3+ Tregs in the spleen and MLN (FIGS. 5 and 6). FIG. 5 demonstrates that Helminths increase the percentage of donor and recipient FoxP3+ Tregs. Spleen and MLN cells from uninfected control and helminth-infected mice were stained for CD3, CD4, H2b, H2d and FoxP3. Representative dot plots from spleen (upper row) and MLN (lower row) cells isolated from uninfected control and *H. bakeri* (polygyrus)-infected mice 6 days after BMT. Cells are gated on donor (left and middle columns) or recipient (right column) CD3+ T cells. The percentage of FoxP3+ CD4 T cells are displayed in each dot plot.

FIG. 6 presents data showing that Helminths increase the number of splenic and MLN FoxP3+ Tregs. The percentage of donor and recipient, splenic and MLN FoxP3+ Tregs from uninfected control and *H. bakeri* (polygyrus)-infected mice was analyzed as described in FIG. 5. The number of FoxP3+ splenic donor or recipient Tregs per mouse was calculated using the total number of cells isolated from uninfected control and *H. bakeri* (polygyrus)-infected mice 6 days after BMT and the percentage of FoxP3+ CD4+ recipient or donor cells gated on CD3+ lymphocytes (N=Number of mice for the analysis of splenic FoxP3+ Tregs and N=Number of experiments, each utilizing cumulative cells from multiple mice for MLN FoxP3+ Tregs). Data are displayed as mean±SEM (*$p<0.05$ btw uninfected control and *H. bakeri* (polygyrus)-infected spleen or MLN FoxP3+ donor Treg percentage and total number). As we did not analyze the FoxP3+ recipient Treg percentage and number from uninfected mice due to low numbers of events, no statistical analysis was performed between uninfected control and *H. bakeri* groups for percentage and number of recipient FoxP3+ Tregs. The number of FoxP3+MLN donor or recipient Tregs per mouse was calculated using the total number of mice utilized in each experiment, the total number of cells isolated from pooled MLN cells of uninfected control and *H. bakeri*-infected mice and the percentage of FoxP3+ CD4+ cells gated on CD3+ lymphocytes.

Figure 13:
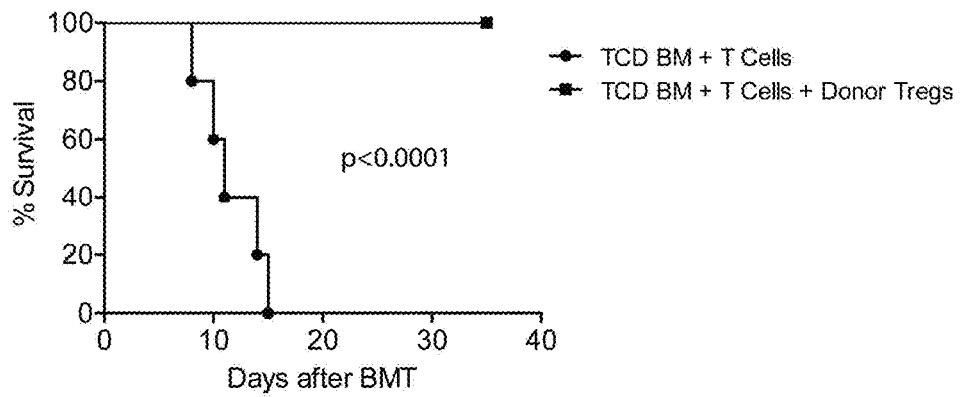
FIG. 13 demonstrates that donor CD25+ CD4 T cells enriched for FoxP3+ Tregs control mortality, related to acute GVHD. Acute GVHD was induced in lethally irradiated Balb/C recipients by transfer of $10 \times 10^6$ C57BL/6 TCD BM and $1.5 \times 10^6$ donor T cells per recipient, as detailed herein. A parallel group of mice was additionally administered $1.5 \times 10^6$ donor CD4+ CD25+ splenic T cells enriched for FoxP3+ Tregs. Mice were observed daily. The difference in survival between the groups was determined by Kaplan Meier analysis (N=5 for TCD BM+ splenic T cells and N=5 for TCD BM+splenic T cells+donor CD4+ CD25+ cells; $p<0.0001$).

The number of recipient-derived T cells from uninfected Balb/C mice was too low to analyze for FoxP3 (FIG. 3). Donor CD25+ CD4 T cells enriched for FoxP3+ Tregs regulated acute GVHD, when co-transferred with conventional T cells (FIG. 13).

Example 5

Figure 7:
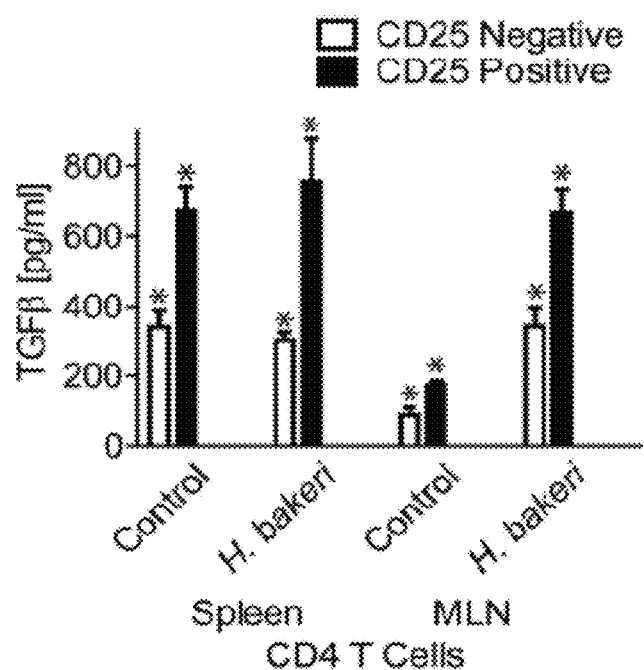
FIG. 7 is a graph demonstrating that Treg enriched T cell fractions generate more TGFβ compared to Treg depleted T cell populations. TGFβ output of plate-bound anti-CD3 and soluble anti-CD28 stimulated splenic and MLN CD25- enriched or depleted CD4+ T cells from 3 week *H. bakeri* (polygyrus) colonized or uninfected control Balb/C mice without BMT was measured by ELISA from the cell culture supernatants. Data are representative examples from at least 3 independent experiments for each CD25 negative and CD25 positive pairs of lymphocyte isolates (*p<0.001 between CD25 negative and CD25 positive CD4 T cells).

CD4 T Lymphocytes Enriched for FoxP3+ Tregs Generate More TGFβ than Other Peripheral CD4 T Cells Most FoxP3+ CD4 T cells are found in the CD25+ CD4+ T cell compartment (FIG. 14). Plate-bound anti-CD3 and soluble anti-CD28-stimulated splenic and MLN CD4+ CD25+ T cells from *H. bakeri* (polygyrus)-infected or uninfected Balb/C mice generated ~2-fold more TGFβ compared to the CD4+ CD25− T cell fraction, as shown by ELISA from supernatants harvested 48 hours after stimulation (FIG. 7). The TGFβ cytokine content in anti-CD3/28 stimulated T cell depleted parallel cultures was <20 pg/ml and did not increase with anti-CD3/28 stimulation (data not shown).

Example 6

Figure 8:
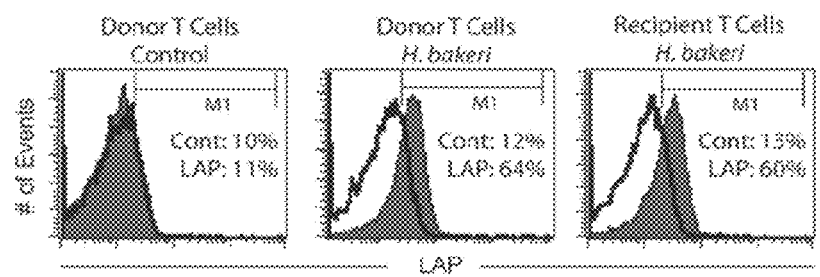
FIG. 8 presents histograms demonstrating that Helminth infection increases the frequency of latency associated peptide (LAP) positive T cells during GVHD. Display of total splenic CD3+ T cell LAP (filled histograms) expression with isotope control (Cont; empty histograms), in uninfected control (left) and *H. bakeri* (polygyrus)-infected (middle and right) mice, six days after BMT. Cells were gated on donor H2b+ (left and middle) or recipient H2d+ (right) lymphocytes. Data are representative example from independent experiments utilizing cumulatively 9 uninfected control and 9 *H. bakeri*-infected mice. Percentage of events in M1 gate was displayed.

Helminth Infection is Associated with Enrichment of Latency Associated Peptide (LAP) Positive Donor and Recipient T Cells During GVHD Prepro-TGFβ peptide is cleaved into N-terminal latency associated peptide (LAP) and C-terminal TGFβ protein after transcription and translation (Li, M. O., Wan, Y. Y., Sanjabi, S., Robertson, A. K., and Flavell, R. A. 2006 Annu. Rev. Immunol.:99-146. Chen, M. L., Yan, B. S., Bando, Y., Kuchroo, V. K., and Weiner, H. L. 2008. J. Immunol.:7327-7337). LAP is expressed on T cells that may regulate immune responses in a TGFβ-dependent manner (Chen et al., Supra). LAP expression on donor and recipient T cells during acute GVHD was determined. Splenic T cells in helminth-infected recipients displayed increased LAP expression on donor or recipient-derived CD3+ T lymphocytes (FIG. 8). MLN recipient T cell LAP staining in helminth-infected mice and MLN donor T cell LAP expression in uninfected control or *H. bakeri* (polygyrus)-administered mice was high and did not differ between groups (data not shown). These results indicated that *H. bakeri* (polygyrus) infection was associated with survival of LAP+ recipient T cells during acute GVHD.

Example 7

Helminths Regulate GVHD in a TGFβ-Dependent Manner

Figure 9:
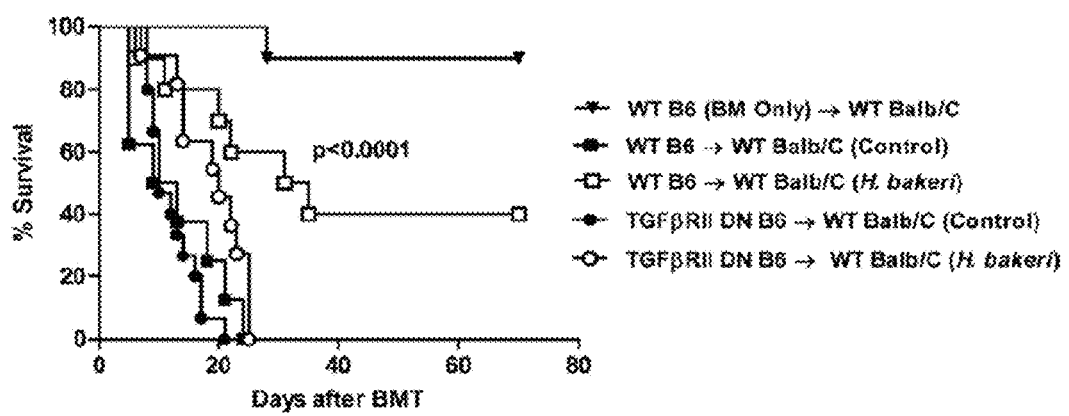
FIG. 9 demonstrates that Helminths regulate donor T cell-mediated GVHD in a TGFβ-dependent manner. Kaplan Meier survival curves of uninfected Balb/C recipients transferred TCD-BM cells only from uninfected C57BL/6 mice (triangles), uninfected Balb/C recipients transferred TCD-BM cells and total splenic T cells from uninfected C57BL/6 mice (closed squares), uninfected Balb/C recipients transferred TCD-BM cells from uninfected C57BL/6 WT and splenic T cells from uninfected TGFβRII DN mice (closed circles), *H. bakeri* (polygyrus)-infected Balb/C recipients transferred TCD-BM and splenic T cells from uninfected C57BL/6 mice (open squares) and *H. bakeri* (polygyrus)-infected Balb/C recipients transferred TCD-BM cells from uninfected C57BL/6 mice and splenic T cells from uninfected TGFβRII DN mice (open circles). Cumulative data from three independent experiments with multiple mice from each group (p<0.0001).
Figure 10A:
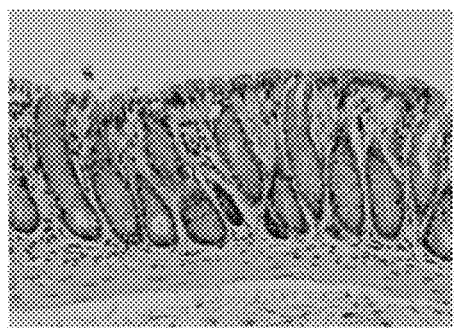
FIGS. 10A-D demonstrates that *H. bakeri* infection is not associated with inflammatory changes in the colon or lungs. Colons (A) and lungs (C) from control (left) and colons (B) and lungs (D) from helminth-infected (right) mice without BMT were isolated, fixed and histopathological analysis was performed in 6 μm thick sections under low (10×) (A and D) power of magnification. Inflammatory changes were analyzed as described in Methods.
Figure 10B:
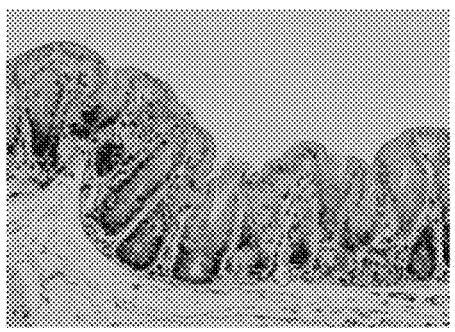
Figure 10C:
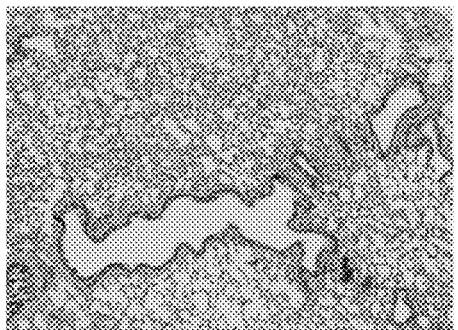
Figure 10D:
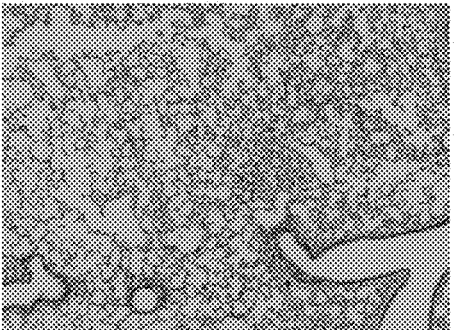

TGFβ is a strong regulator of Th1 immunity (Shlomchik, Supra; Izsue et al., Supra; Chen et al., Supra; Banovic, T., Macdonald, K. P., Morris, E. S., Rowe, V., Kuns, R., Don, A., Kelly, J., Ledbetter, S., Clouston, A. D., and Hill, G. R. 2005 Blood:2206-2214). As helminth infection suppressed Th1 inflammation during GVHD, thereby increasing the number of T cells that secrete TGFβ and express LAP, the ability of helminths to regulate the donor T cell-mediated GVHD in a TGFβ-dependent manner was determined. Donor T cells from uninfected TGFβRII DN mice (H2b), in which the T cells are unresponsive to TGFβ-mediated immune regulation due to T cell-specific over-expression of a truncated TGFβ receptor II (Gorelik, L., and Flavell, R. A. 2000. Immunity. 171-181) were used. Because the engineered CD4 promoter driving the truncated TGFβRII expression lacked the CD8 silencer, the CD4 and CD8 T cells in these mice are unresponsive to TGFβ-mediated immune regulation. Uninfected control and *H. bakeri* (polygyrus)-infected recipient WT Balb/C mice were given T cell depleted (TCD)-BM cells from C57BL/6 WT donors and splenic T cells from TGFβRII DN mice (FIG. 9). Other groups included uninfected Balb/C recipients given TCD-BM cells from uninfected C57BL/6 mice and uninfected control or *H. bakeri* (polygyrus)-infected recipient Balb/C recipients given TCD-BM and splenic T cells from C57BL/6 WT donors. Transfer of TCD-BM cells was associated with survival of 90% of mice, while GVHD was uniformly lethal in uninfected Balb/C recipients that also received C57BL/6 WT or TGFβRII DN splenic T cells (FIG. 9). Strikingly, 40% of *H. bakeri* (polygyrus)-infected recipients that received T cells from WT C57BL/6 mice survived the GVHD, while *H. bakeri* (polygyrus) infection did not protect against GVHD lethality in recipients that received TGFβRII DN splenic T cells (FIG. 9).

Example 8

Administration of Helminths to a Human Subject Following a Transplant Prevents Acute GVHD Following transplantation, a helminithic parasite preparation according to the invention is administered to a subject. Useful helminthic parasites include, but are not limited to, two groups. The first group is helminthic parasites that naturally colonize humans and the second group is helminthic parasites that colonize non-human mammals, but protect humans against inflammatory disease.

A preparation of parasites that colonize non-human mammals useful for the methods of the invention is obtained as follows. A non-human mammal is Infected, for example, with 1000 to 1500 cercariae or with *Trichuris suis* ova. The infection is allowed to mature (6 to 7 weeks). Livers are removed from the animals and placed in 600 mOsm sterile phosphate buffered saline containing 5% glucose, 100 U/ml penicillin and 100 mg/ml streptomycin. The livers are allowed to autodigest for 24 hours at room temperature and are then pulse homogenized at low speed for 3 minutes in a cold Waring blender. The homogenate is incubated with collagenase (2 mg/ml) and trypsin (2 mg/ml) at 32° C. for one hour. The homogenate is filtered through 50 and 80-100 mesh sieves to remove clumps of tissue and debris. The eggs are recovered from the filtrate by passing the filtrate over a 325 mesh sieve. The eggs do not pass through the screen. The eggs are flushed off of the screen and into a 50 ml polypropylene centrifuge tube. The eggs are washed by repeated low speed (400×g) centrifugation in sterile phosphate buffered saline with 5% glucose. All collagenous debris is removed from the eggs. An aliquot of eggs in a 1 ml Sedwick chamber is used to determine total egg number. Isolated eggs are suspended in saline and flash frozen in liquid nitrogen without cryoprotectant to kill the eggs.

Helminthic parasites that are used are *Trichuris muris, Trichinella spiralis, Nippostrongylus prasiliensis, Heligmonsomoides polygyrus, Hymenolepsis nanan, Angiostrongylus* species, *Trichuris suis, Ascaris suum, Trichuris vulpis, Toxocara* species, *Gnathostoma* species, *Ancylostoma* species, *Anisakis* species and *Pseudoterranova* species.

Washed eggs are resuspended at 50,000 eggs/ml of phosphate buffered saline. This preparation is transferred to a glass tissue homogenizer. The eggs are homogenized on ice. To insure that all shells are broken and miracidia are disrupted, an aliquot (5 ml) is removed for microscopic inspection. The homogenate is transferred to ultracentrifuge tubes and centrifuged at 100,000×g for 2 hours at 4° C. The aqueous fraction (SEA) is recovered and the protein content is determined. The SEA is stored in small aliquots at −70° C. Eggs or soluble egg components are used to initiate Th2 responses or to boost Th2 responses previously initiated by colonization with viable helminths.

Helminiths (e.g., egg, cercariae or larvae) can be administered orally or parenterally. Alternatively, soluble worm or egg extracts are given orally or parenterally to the subject.

Thawed eggs are administered orally or parenterally, for example by subcutaneous, intramuscular or intravenous injection at sites of Th1 inflammation to elicit strong Th2 responses.

The amount of Helminthic preparation administered to the subject ranges from about 50 parasites total to about 50,000 parasites total.

The parasite preparation is administered daily, weekly, bi-weekly, every two weeks or at decreasing intervals after transplant as indicated by analysis of the symptoms of GVHD. The duration of treatment is at least 6 months and may be continued for the lifetime of a subject.

Human subjects are examined for acute GVHD symptoms including, but not limited to onset of a skin rash, diarrhea and weight loss or anorexia prior to, during and following treatment. GVHD is diagnosed by laboratory studies including Complete Blood Count (CBC), liver function tests and determination of serum electrolytes and chemistry, in combination with art accepted methods of disease staging discussed herein above. If indicated, diagnosis is also done by invasive methods including (1) tissue biopsy to determine the disease state of skin, upper or lower GI system, and/or liver; and/or (2) barium swallow studies, upper GI endoscopy, sigmoidoscopy and/or colonoscopy to diagnose GI disorders.

GVHD is also diagnosed by determining one or more of the level of production of IFN$\gamma$ and/or TNF$\alpha$ by donor regulatory T cells isolated from the subject after transplantation, the level of IFN$\gamma$ and/or TNF$\alpha$ in the serum of the subject, the number of latency associated protein expressing donor and/or recipient T cells in the subject, and the number and/or percent of FoxP3+ donor and/or recipient derived regulatory T cells in the subject. GVHD is assessed by any of the methods presented herein above in the section entitled: "GVHD".

Example 8

Administration of Helminths to a Human Subject Prior to a Transplant Prevents GVHD A helminthic parasite preparation according to the invention is administered to the subject prior to transplantation as described in Example 7. The parasite preparation is administered 2 months or less, (e.g., 2 months, 1 month, 3 weeks, 2 weeks, 1 week, 72 hours, 48 hours, 24 hours or less) prior to transplantation. GVHD is diagnosed as in Example 7. Treatment may be continued after transplantation as described in Example 7.

Example 10

Administration of Helminths to a Human Subject to Treat Post-Transplantation GVHD A helminthic parasite preparation according to the invention is administered to a subject diagnosed with GVHD following a transplant as described in Example 7. Treatment of GVHD is determined by analysis of any of the symptoms described in Example 7 and in the section entitled "GVHD". The GVHD symptoms are assessed according to any of the symptoms described in Example 7 and in the section entitled "GVHD".

Example 11

In Vivo Assessment of Graft Versus Tumor (GVT) Activity

Luciferase expressing syngeneic leukemia/lymphoma cells (A20-luc; H2d) were administered to helminth-infected or uninfected control recipient mice (H2d) that received bone marrow depleted T cells or bone marrow depleted T cells plus splenic donor T cells from C57BL/6 (H2b) donors. Luciferase activity was measured for 70 days at regular intervals, using an IVIS 100 imaging system (Caliper Life Sciences, Hopkinton, Mass.). At each time point of analysis, luciferin was administered 5 minutes prior to the analysis intraperitoneally. A second luciferin injection and IVIS imaging was performed in mice that exhibited a negative first luciferase activity.

FIG. 11 presents data demonstrating that no GVHD-related changes were evident in $H.$ $bakeri$-infected or control mice that underwent T cell depleted bone marrow (TCD BM) transfer. The weight change in helminth-infected (open squares) and uninfected (closed squares) mice were plotted for 10 weeks after TCD BM transfer (A, left). The disease score of uninfected control (closed squares) and $H.$ $bakeri$-infected mice (open squares) were taken weekly over the entire course of the experiment (A, right). Colons and lungs from control (B, left) and helminth-infected (B, right) mice were isolated 6 days after TCD BM transfer. Histopathological analysis was performed in 6 μm thick sections under low (10×) power of magnification. Inflammatory changes were analyzed as described in Methods.

FIG. 15 demonstrates that Helminths do not interfere with GVT. (A) TCD BM transferred uninfected or helminth-infected mice displayed significant tumor activity while no tumor was evident in helminth-infected mice that survived GVHD (TCD BM+ SpI T cells ($H.$ $bakeri$)). (B) Kaplan Meier analysis showing helminthic protection from GVHD and tumor challenge (p<0.05 between TCD BM+ T cells ($H.$ $bakeri$) and other groups.

Example 12

Figure 16:
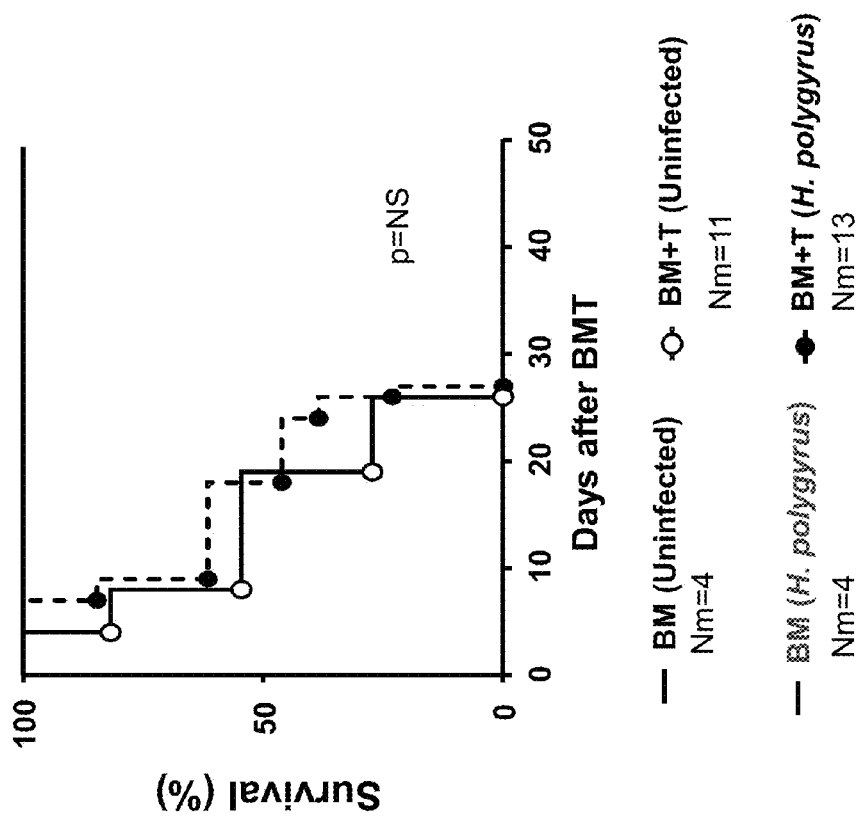
FIG. 16 demonstrates that Helminthic regulation of serum TH1 cytokine generation is STAT6 dependent.
Figure 17:
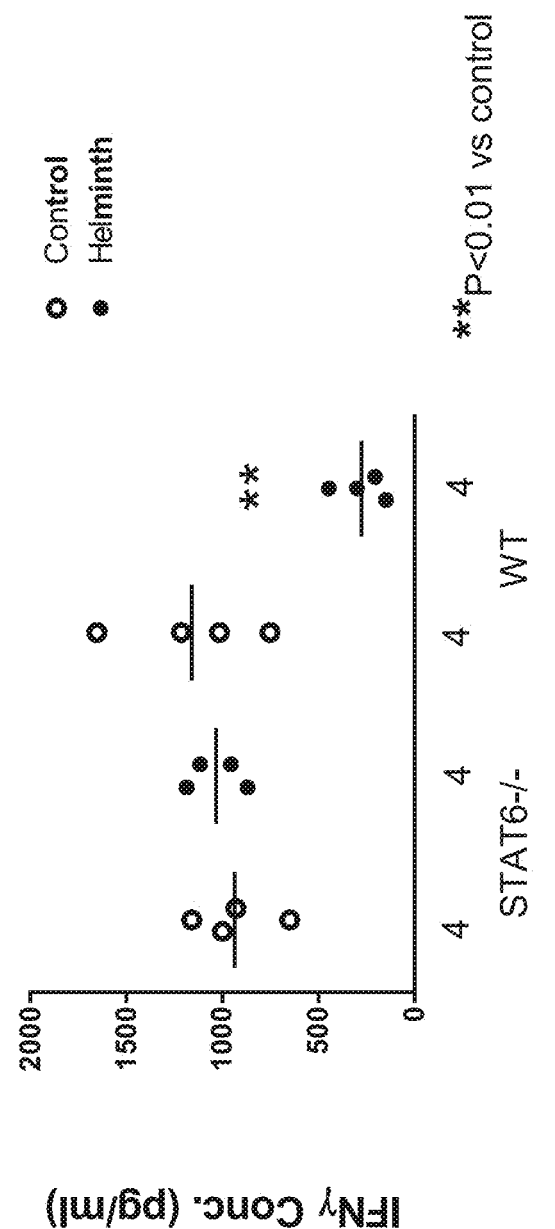
FIG. 17 demonstrates that Helminths do not increase the percent survival of STAT6−/− mice.

Helminths Increase the Percentage of Donor and Recipient FoxP3+ Regulatory T Cells in a STAT6 Dependent Manner The STAT6 gene encodes a transcription factor that is involved in the regulation of cytokine production. Parallel groups of uninfected control and $H.$ $bakeri$ (polygyrus)-administered wild type mice (Balb/C) and STAT6−/− mice (The Jackson Laboratory; Stock Number 002828 (Strain Name: C.129S2-Stat6$^{tm1Gru}$/J) were analyzed. Acute GVHD was initiated in uninfected control or 3 week $H.$ $bakeri$ (polygyrus)-infected irradiated Balb/C or STAT6−/− recipients by transfer of total splenic T cells and T cell depleted (TCD)-BM cells from uninfected donor C57BL/6 mice. Replicate samples of mice received only TCD-BM. Helminth infection led to a significant increase in the percentage and number of donor as well as recipient FoxP3+ regulatory T cells in the spleen and MLN of wild type mice but not STAT6−/− mice (See Table 1). FIG. 16 demonstrates that Helminithic regulation of serum Th1 cytokine (IFN$\gamma$) generation is STAT6 dependent. As shown in FIG. 16, there is a decrease in the concentration of IFN$\gamma$ in the serum of wild type mice that have been administered *H. bakeri* (polygyrus) but not in the serum of STAT6−/− mice that have been administered *H. bakeri* (polygyrus). As demonstrated in FIG. 17, there is no significant difference in the percent survival of STAT6−/− mice that have been administered *H. bakeri* (polygyrus) as compared to STAT6−/− mice that have not been administered *H. bakeri* (polygyrus).

TABLE 1

Helminths increase the percentage and number of donor and recipient Foxp3+CD4 Regulatory T Cells in GVHD wild type mice but not in STAT6−/− mice.

| WT Organ | CD3+T cell type | Foxp3+CD4 Treg percentage | | | Foxp3+CD4 Treg number | | |
|---|---|---|---|---|---|---|---|
| | | Uninfected | *H. polygyrus* | P value | Uninfected | *H. polygyrus* | P value |
| Spleen | Donor | $0.62 \pm 0.25$ | $1.52 \pm 0.83$ | $P < 0.05$ | $1.5 \pm 1.1 \times 10^4$ | $3.3 \pm 1.7 \times 10^4$ | $P < 0.05$ |
| (n = 7) | Recipient | $2.75 \pm 1.25$ | $4.97 \pm 2.36$ | $P < 0.05$ | $2.6 \pm 2.2 \times 10^3$ | $18.0 \pm 1.5 \times 10^3$ | $P < 0.05$ |
| MLN | Donor | $0.4 \pm 0.1$ | $2.2 \pm 09$ | $P < 0.001$ | $0.3 \pm 0.2 \times 10^3$ | $2.1 \pm 1.0 \times 10^3$ | $P < 0.01$ |
| (n = 6) | Recipient | $8.6 \pm 3.6$ | $14.1 \pm 3.3$ | $P < 0.05$ | $0.4 \pm 0.3 \times 10^3$ | $4.7 \pm 2.6 \times 10^3$ | $P < 0.01$ |

| STAT6−/− Organ | CD3+T cell type | Foxp3+CD4 Treg percentage | | |
|---|---|---|---|---|
| | | Uninfected | *H. polygyrus* | P value |
| Spleen | Donor | $0.02 \pm 0.0$ | $0.052 \pm 0.01$ | $P < 0.05$ |
| | Recipient | $0.0004 \pm 0.00$ | $0.001 \pm 0.00$ | $P < 0.05$ |
| MLN | Donor | $0.20 \pm 0.04$ | $0.14 \pm 0.00$ | N/A |
| | Recipient | $0.04 \pm 0.01$ | $0.17 \pm 0.02$ | $P < 0.01$ |

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the

The invention claimed is:

1. A method of decreasing the production of IFNγ and/or TNFα by donor T cells in a subject that has received a transplant, comprising administering a helminthic parasite preparation to the subject in an amount and for a time effective to decrease said production, wherein at least one selected from the group consisting of a graft versus tumor effect, a graft versus leukemia effect, a graft versus lymphoma effect, a graft versus B cell neoplasm effect, and a graft versus myeloma effect is observed in the subject.

2. The method of claim 1, wherein said graft versus myeloma effect is observed in said subject.

3. The method of claim 1, wherein the parasite preparation is administered daily, weekly, bi-weekly or every two weeks after the transplant or wherein the parasite preparation is administered in decreasing intervals of time following the transplant.

4. The method of claim 1, wherein administration is continued for at least 6 months.

5. The method of claim 1, wherein the parasite preparation is administered to the subject after the subject has developed graft versus host disease (GVHD).

6. The method of claim 1, wherein GVHD is acute or chronic.

7. The method of claim 1, wherein GVHD is treated if following administration:
   (a) the subject does not have an onset of one or more of a symptom of GVHD selected from the group consisting of: skin rash, diarrhea, liver disease, weight loss/anorexia, nausea, and vomiting;
   (b) there is no increase in the level of IFNγ in the serum of the subject;
   (c) there is no increase in the level of IFNγ in the serum of the subject and no onset of a symptom of GVHD selected from the group consisting of: skin rash, diarrhea, liver disease, weight loss/anorexia, nausea, and vomiting; and/or
   (d) there are no detectable apoptotic bodies in tissue derived from the upper gastrointestinal tract.

8. The method of claim 1, wherein the level of IFNγ and/or TNFα in the serum of the subject is measured prior to administration of the parasite preparation and after administration.

9. The method of claim 1, wherein the number of latency associated protein (LAP) expressing recipient T cells of the subject following administration of the parasite preparation as compared to the level before administration, indicates prevention of GVHD.

10. The method of claim 1, wherein the number of LAP expressing recipient T cells of the subject is measured prior to administration of the parasite preparation.

11. The method of claim 1, wherein administration is continued for at least 6 months after transplant.

12. The method of claim 1, wherein the transplant is a bone marrow transplant.

13. The method of claim 1, wherein the parasite preparation comprises 500-7500 parasites.

14. The method of claim 1, wherein the parasite preparation is administered orally.

15. The method of claim 1, wherein the parasite preparation is administered in combination with a second agent.

16. The method of claim 1, wherein the helminth is selected from the group consisting of: helminths that colonize humans; and helminths that colonize non-human mammals.

17. The method of claim 1, wherein said graft versus tumor effect is observed in said subject.

18. The method of claim 1, wherein said graft versus leukemia effect is observed in said subject.

19. The method of claim 1, wherein said graft versus lymphoma effect is observed in said subject.

20. The method of claim 1, wherein said graft versus B cell neoplasm effect is observed in said subject.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: artificial
<220> FEATURE:
<223> OTHER INFORMATION: primer

<400> SEQUENCE: 1
cccaggaaag acagcaacct t                                                 21

<210> SEQ ID NO 2
<211> LENGTH: 21
<212> TYPE: DNA
<213> ORGANISM: artificial
<220> FEATURE:
<223> OTHER INFORMATION: primer

<400> SEQUENCE: 2
ttctcacaac caggccactt g                                                 21

<210> SEQ ID NO 3
<211> LENGTH: 28
<212> TYPE: DNA
<213> ORGANISM: artificial
<220> FEATURE:
<223> OTHER INFORMATION: synthetic construct

<400> SEQUENCE: 3
atcctaccca ctgctggcaa atggagtc                                          28

<210> SEQ ID NO 4
<211> LENGTH: 20
<212> TYPE: DNA
<213> ORGANISM: artificial
<220> FEATURE:
<223> OTHER INFORMATION: synthetic oligonucleotide

<400> SEQUENCE: 4
tccatgacgt tcctgacgtt                                                   20
```